(12) United States Patent
Rainey et al.

(10) Patent No.: US 7,742,829 B2
(45) Date of Patent: Jun. 22, 2010

(54) ELECTRODE ARRANGEMENT FOR APPLYING ELECTRICAL SIGNALS TO THE SKIN OF AN ANIMAL

(75) Inventors: Christopher J. Rainey, Devon (GB); John P. Southgate, Devon (GB); Andrea Moretti, London (GB); Richard Nagle, London (GB)

(73) Assignee: Wound Solutions Limited, London (GB)

( * ) Notice: Subject to any disclaimer, the term of this patent is extended or adjusted under 35 U.S.C. 154(b) by 564 days.

(21) Appl. No.: 11/138,358

(22) Filed: May 27, 2005

(65) Prior Publication Data
US 2006/0173523 A1    Aug. 3, 2006

(30) Foreign Application Priority Data
Feb. 1, 2005    (GB)    ................. 0502070.6

(51) Int. Cl.
*A61N 1/32* (2006.01)
(52) U.S. Cl. ........................... 607/152; 607/50
(58) Field of Classification Search ............ 600/14, 600/392
See application file for complete search history.

(56) References Cited

U.S. PATENT DOCUMENTS

| | | | |
|---|---|---|---|
| 3,472,233 A | | 10/1969 | Sarbacher |
| 3,989,035 A | | 11/1976 | Zuehlsdorff |
| 4,082,086 A | | 4/1978 | Page et al. |
| 4,117,846 A | | 10/1978 | Williams |
| 4,353,372 A | | 10/1982 | Ayer |
| 4,398,545 A | | 8/1983 | Wilson |
| 4,556,051 A | * | 12/1985 | Maurer ............. 600/14 |
| 4,635,641 A | | 1/1987 | Hoffman |
| 4,686,995 A | | 8/1987 | Fournial et al. |

(Continued)

FOREIGN PATENT DOCUMENTS

DE    83 05 103    6/1988

(Continued)

OTHER PUBLICATIONS

Axelgaard Manufacturing Co., Ltd. Brochure "Neuorostimulation Electrodes Stimulation Comfort Through Advanced Technology", 2004-2005 Product Guide, Feb. 2004.

(Continued)

*Primary Examiner*—Carl H. Layno
*Assistant Examiner*—Jon-Eric C. Morales
(74) *Attorney, Agent, or Firm*—Dickstein Shapiro LLP

(57) ABSTRACT

An electrode arrangement for applying electrical signals to skin of an animal comprising a flexible electrically non-conductive substrate, at least one electrode provided on a first surface of the substrate for applying electrical signals to the skin when placed on the skin, at least one connector connected to a respective electrode for providing electrical signals to the respective electrode and an electrically non-conductive sealing arrangement connected to the substrate for sealing the substrate and the skin to prevent ingress of moisture to the at least one electrode and to the at least one connector at the connection to the respective electrode. The or each electrode comprises a plurality of spaced electrically conductive elements to allow flexion of the electrode arrangement and electrically conductive material between the plurality of spaced electrically conductive elements to form a two-dimensional electrically conductive path across at least a portion of the first surface of the substrate.

24 Claims, 24 Drawing Sheets

U.S. PATENT DOCUMENTS

| | | | |
|---|---|---|---|
| 4,738,250 | A | 4/1988 | Fulkerson et al. |
| 4,895,154 | A | 1/1990 | Bartelt et al. |
| 4,982,742 | A | 1/1991 | Claude |
| 5,158,081 | A | 10/1992 | McWhorter et al. |
| 5,218,973 | A | 6/1993 | Weaver et al. |
| 5,263,481 | A * | 11/1993 | Axelgaard ............ 600/392 |
| 5,336,255 | A | 8/1994 | Kanare et al. |
| 5,395,398 | A | 3/1995 | Rogozinski |
| 5,433,735 | A | 7/1995 | Zanakis et al. |
| 5,450,845 | A | 9/1995 | Axelgaard |
| 5,511,548 | A | 4/1996 | Riazzi et al. |
| 5,536,446 | A | 7/1996 | Uy et al. |
| 5,904,712 | A | 5/1999 | Axelgaard |
| 5,974,342 | A | 10/1999 | Petrofsky |
| 5,974,344 | A | 10/1999 | Shoemaker, II |
| 6,002,965 | A | 12/1999 | Katz et al. |
| 6,282,448 | B1 | 8/2001 | Katz et al. |
| 6,393,326 | B1 | 5/2002 | Nachum |
| 6,728,577 | B2 * | 4/2004 | Minogue et al. ............ 607/48 |
| 6,731,987 | B1 | 5/2004 | McAdams et al. |
| 6,788,979 | B1 | 9/2004 | Axelgaard et al. |
| 2002/0103513 | A1 * | 8/2002 | Minogue et al. ............ 607/46 |
| 2003/0050675 | A1 | 3/2003 | Nachum |
| 2003/0144723 | A1 | 7/2003 | Andino et al. |
| 2004/0015223 | A1 | 1/2004 | Andino et al. |
| 2004/0054384 | A1 | 3/2004 | Nachum |
| 2004/0147977 | A1 | 7/2004 | Petrofsky |
| 2004/0158305 | A1 | 8/2004 | Axelgaard |
| 2004/0176675 | A1 | 9/2004 | Rice et al. |

FOREIGN PATENT DOCUMENTS

| | | | |
|---|---|---|---|
| EP | 0243 053 | | 10/1987 |
| EP | 0 367 320 | A1 | 5/1990 |
| GB | 2 148 717 | | 6/1985 |
| GB | 2 185 403 | | 7/1987 |
| GB | 2 404 858 | | 2/2005 |
| GB | 2 406 519 | A | 4/2005 |
| WO | WO 90/09810 | | 9/1990 |
| WO | WO 90/11796 | | 10/1990 |
| WO | WO 94/26350 | | 11/1994 |
| WO | WO 99/04852 | | 2/1999 |
| WO | WO 99/15101 | | 4/1999 |
| WO | WO 99/64105 | | 12/1999 |
| WO | WO 00/27467 | A1 | 5/2000 |
| WO | WO 01/03768 | A1 | 1/2001 |
| WO | WO 01/91697 | A2 | 12/2001 |
| WO | WO 02/056960 | A2 | 7/2002 |
| WO | WO 02/089667 | | 11/2002 |
| WO | WO 02/089911 | A1 | 11/2002 |
| WO | WO 02/098502 | A2 | 12/2002 |
| WO | WO 2004/049937 | A1 | 6/2004 |
| WO | WO 2004/071274 | A2 | 8/2004 |
| WO | WO 2005/004983 | A2 | 1/2005 |
| WO | WO 2005/023361 | A2 | 3/2005 |
| WO | WO 2005/032652 | A1 | 4/2005 |

OTHER PUBLICATIONS

Electrode Pad manufactured by Axelgaard.

R.J. Abboud et al., "Lower limb muscle dysfunction may contribute to foot ulceration in diabetic patients", Clinical Biomechanics, vol. 15, Issue 1, Jan. 2000, pp. 37-45.

Axelgaard Manufacturing Co., Ltd., Muscle Stimulation & TENS Electrodes with MultiStick Gel, http://www.axelgaard.com/palsplat.html, Nov. 18, 2004.

Axelgaard Manufacturing Co., Ltd., Neurostimulation Electrodes Stimulation Comfort Through Advanced Technology, 2004-2005 Product Guide.

P.E. Houghton et al., "Effect of Electrical Stimulation on Chronic Leg Ulcer Size and Appearance", Physical Therapy, vol. 83, No. 1, Jan. 2003.

L.C. Kloth., "Electrical Stimulation for Wound Healing: A Review of Evidence From In Vitro Studies, Animal Experiments, and Clinical Trials", Lower Extremity Wounds 4(1), 2005, pp. 23-44.

L.A. Lavery et al., "Reducing Dynamic Foot Pressure in High-Risk Diabetic Subjects With Foot Ulcerations. A Comparison of Treatments", Diabetes Care, vol. 19, Issue 8, American Diabetes Assoc., 1996.

J.J. Wertsch et al., "Plantar Pressures With Total Contact Casting", Journal of Rehabilitation Research and Development, vol. 32, No. 3, Oct. 1995, pp. 205-209.

M. Butcher, "How to Use POSiFECT® Bio-Electric Stimulation Therapy in Chronic Wounds", Wound Essentials, vol. 2, 2007, pp. 186-193.

* cited by examiner

ELECTRODE ARRANGEMENT FOR APPLYING ELECTRICAL SIGNALS TO THE SKIN OF AN ANIMAL

The present invention relates to an electrode arrangement for applying electrical signals to the skin of an animal such as a human.

BACKGROUND OF THE INVENTION

It is well documented that that the process of healing, growth and regeneration in living tissue is brought about by the flow of the body's own natural electrical current. Assisting the human body's natural healing tissue by applying electrical signals to the body in a form of therapy known as electrotherapy has been described in various publications. Electrotherapy is used in wound healing, pain treatment and muscle stimulation.

Effective electrotherapy requires the use of suitable electrodes or pads for administering electrical signals to the skin. For treatment to be successful, electrodes must be effectively electrically coupled to the skin. Accomplishing such an effective coupling is not evident when applying electrodes to uneven skin surface and curved body parts. Any such electrode device must therefore be sufficiently flexible to accommodate the curvaceous nature of the human body and to accommodate relative movement of patients skin during therapy. Precise placement of electrodes on the body is another important requirement influencing the outcome of treatment.

Various electrodes for application of electrical signals to the skin have been proposed.

U.S. Pat. No. 5,450,845 describes a medical electrode system which includes a flexible electrically conductive patch disposed on an electrically non-conductive backing material. The basic electro-conducting and electrical distribution portion of the electrode is washable and reusable. A separate disposable, adhesive, electrical conductive pad is used to couple this portion to the skin. One embodiment of the invention described uses a plurality of electrodes and a system for insuring proper placement of the electrode set on the body part.

U.S. Pat. No. 6,788,979 describes an electrical stimulation compress kit which allows for precise repeatable positioning of stimulation pads onto a body part. The device includes a flexible member for contacting a body part and hook/loop members for tightly supporting the flexible member against the body part.

The above systems suffer from the disadvantages that they are not effectively sealed against the ingress of moisture to exposed electrically conductive components of the electrode and that they must be connected to external leads and current generators in order to operate.

SUMMARY OF THE INVENTION

The present invention provides an electrode arrangement and a method for applying electrical signals to skin of an animal such as a human.

In one aspect of the invention, the electrode arrangement includes a flexible electrically non-conductive substrate, one or more electrodes provided on a first surface of the substrate for applying electrical signals to the skin when placed on the skin, one or more connectors each connected to an individual electrode for providing electrical signals to the respective individual electrode, and an electrically non-conductive sealing arrangement connected to the substrate for sealing the substrate and the skin to prevent ingress of moisture to the at least one electrode and to the at least one connector at the connection to the respective electrode. Thus in accordance with this aspect of the invention, the electrode arrangement is resistant to the ingress of moisture such as urine, perspiration and blood which may lead to electrical short circuits and disruption to the functioning of the electrode system. This is particularly beneficial when using the electrode to perform electrotherapy on patients who may be incontinent or for use in wound healing where the wounds seep plasma or exude infected material.

In one embodiment, the electrically non-conductive sealing arrangement is applied to an edge region of the substrate and disposed around said at least one connector. In another embodiment, the sealing arrangement comprises adhesive material for adhering the substrate to the skin. In a further embodiment, the first surface of the substrate includes a peripheral region where there is no electrode is provided and the adhesive material of the sealing arrangement is applied to this peripheral region. In another embodiment, the sealing arrangement is placed over a second surface of the substrate opposed to said first surface.

In an embodiment of the invention, electrical components are provided on the second surface of the substrate. This arrangement allows electrical connections to be made to the or each electrode on the side of the electrode arrangement not in contact with the skin.

In an embodiment of the invention, each electrode comprises a plurality of interconnected electrically conductive elements to allow flexion of the electrode arrangement. Such an arrangement allows effective electrical coupling to be made between an electrode and the skin even when the surface to which the electrode is being applied is uneven or curvaceous.

In an embodiment of the invention, the plurality of interconnected electrically conductive elements are arranged in a mesh pattern to allow flexion of the electrode arrangement.

In a further embodiment of the invention, the plurality of interconnected electrically conductive elements are arranged in a matrix.

In a further embodiment, the electrode arrangement further comprises electrically conductive gel on the electrode. This arrangement enhances the electrical conductivity across the surface of the electrode and provides further effective electrical coupling between the electrode and the skin.

In an embodiment of the invention, the substrate has a part annular shape. Such an arrangement allows the edge of the electrode arrangement to be placed close to the edges of a wound.

In a further embodiment of the invention the substrate has an annular shape. This arrangement allows the electrode arrangement to be placed on the skin of a patient surrounding a wound.

In an embodiment of the invention the substrate is porous. This arrangement provides an electrode arrangement which is easy to apply and an overall structure which remains effective for longer periods of time.

In a further embodiment of the invention one or more elements of highly electrical resistant material are provided on a surface of the or each electrode. This arrangement provides a more even distribution of electrical current over the surface of the electrode.

In an embodiment of the invention the one or more elements of highly resistant material are interspaced by elements of electrically insulating material thereby allowing isolated packets of high resistance material to be created on the surface of the electrode.

In another embodiment of the invention a device for use with the electrode arrangement according to any embodiment of the invention for absorbing fluid from a wound is provided. The device comprises one or more elements of absorbent material and a plurality of interconnected portions of electrically insulating material interposed between the elements of absorbent material.

In another aspect of the invention, an electrode arrangement for applying electrical signals to skin of an animal includes a flexible electrically non-conductive substrate and at least one electrode provided on a first surface of the substrate for applying electrical signals to the skin when placed on the skin, wherein the substrate includes an extended portion comprising at least one electrically conductive region, the or each electrically conductive regions being in electrical contact with a respective electrode to form a connector to said electrode. Thus in accordance with this aspect of the invention, an electrode arrangement with a low profile connecting lead is provided. The connector being substantially flat will not indent the skin of the patient and help to minimise any discomfort. Furthermore, such an arrangement will not result in raised areas and bulges in bandaging which may be applied over the electrode arrangement during treatment.

In a further aspect of the invention, an electrode arrangement for applying electrical signals to skin of an animal comprises a flexible electrically non-conductive substrate, at least one electrode on a first surface of the substrate for applying electric signals to the skin when placed on the skin, and an electrical generator circuit on a second surface of the said substrate opposed to the first surface of said substrate to apply electrical signals to said at least one electrode. This aspect of the invention provides an electrode arrangement which is self contained and can operate autonomously without the need to be connected to an external electrical current generator in order to function. The electrode arrangement can therefore be used without using cumbersome external leads. Furthermore, the patient undergoing electrotherapy can move around without having to move a separate electrical generator device around with him. Treatment can be thereby be practically implemented over long periods of time without intervention and electrotherapy can be performed on a patient in the comfort of his own home.

In an embodiment, the electric generator circuit is adapted to switch current to flow between different electrodes of the at least three electrodes. This arrangement allows current to be applied through different paths across an injured area of tissue thereby enhancing electrotherapy treatment techniques In another embodiment, the electrical current generator is adapted to switch the direction of current flow between electrodes. This arrangement allows different current profiles to be applied across an area of treatment.

In a further embodiment, the electrical current generator comprises a waveform generator for generating current waveforms across said electrodes. This allows different current waveforms to be applied across the area of treatment and the treatment to be adapted to the patient.

In a further embodiment, the waveform generator is pre-programmed with at least one program to generate a pre-determined waveform or a pre-determined sequence of pre-determined waveforms. Standard treatment programs can therefore be programmed into the system and automatically run, resulting in a user-friendly system.

Another aspect of the invention provides an apparatus for treating a wound comprising a flexible electrically non-conductive substrate, at least three electrodes on a first surface of the substrate for arrangement around the wound, at least three connectors, each connected to a respective electrode adapted to allow current to flow to each of the at least three electrodes when connected to a current generator and an electrical current generator for applying current to said connectors and to switch current between pairs of electrodes. This aspect of the invention provides an apparatus for treating wound in which the electrical current can pass through different paths through the tissue under the wound thereby providing more effective treatment of the wound. Furthermore, since the electrodes are fixed on a common substrate relative position between electrodes does not change during treatment.

A further aspect of the invention provides a method for treating a wound involving placing at least three electrodes on the skin around the wound, applying electrical current between electrodes of the at least three electrodes and switching the current to flow between different electrodes of the at least three electrodes. This aspect of the invention provides a new and improved method whereby electrical current can take different paths across the wound simultaneously or in cycles resulting in an increase in the efficacy of wound healing. Any type of wound such as venous ulcers, pressure sores, diabetic ulcers may be treated using such a method.

Any aspect of the invention can be used in conjunction with another aspect of the invention.

BRIEF DESCRIPTION OF THE DRAWINGS

Embodiments of the invention will now be described with reference to the accompanying drawings, in which.

DESCRIPTION OF THE EMBODIMENTS

Figure 1:
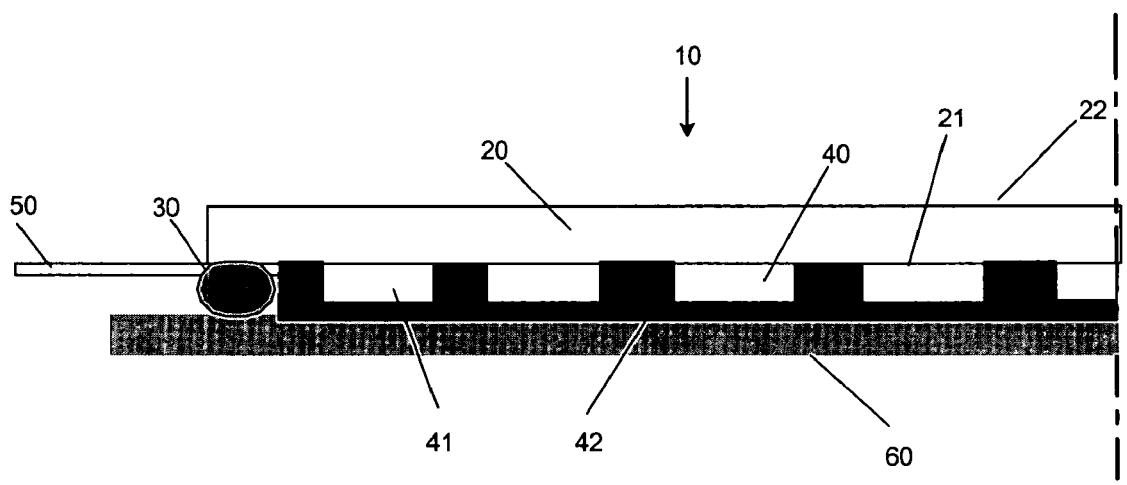
FIG. 1 is a partial cross sectional view of an electrode arrangement according to a first embodiment of the present invention.

FIG. 1 is a partial cross sectional view of an electrode arrangement 10 placed on the skin 60 of a human patient according to a first embodiment of the present invention. The electrode arrangement comprises a flexible electrically non-conducting printed circuit board 20 having a first surface 21 and a second surface 22 opposed to the first surface, electrically non-conductive sealing gel 30, an electrode 40 for applying electrical signals to the skin 60 when placed in contact with the skin and an electrically conductive lead 50 for supplying electrical signals to the electrode 40. The electrode 40 is formed from partial etching of a layer of electrically conductive material, such as gold plated copper, on the first surface 21 of the printed circuit board 20 and comprises electrically conductive tracks 41 with gaps there between. Electrically conductive gel 42 is placed in the gaps between the electrically conductive tracks 41 and over the surface of the electrically conductive tracks 41. The electrically non-conductive gel 30 is waterproof and is placed around the edges of the first surface 21 of the printed circuit board 20 and around the electrically conductive lead 50 adhering the printed circuit board 20 to the skin 60 preventing ingress of moisture such as sweat, urine or blood to the electrode 40 and ingress of moisture to the connection between the electrically conductive lead 50 and the electrode 40 which may lead to short circuits and other undesirable effects. The components of the electrode arrangement are washable so that they may be reused if required.

Figure 2:
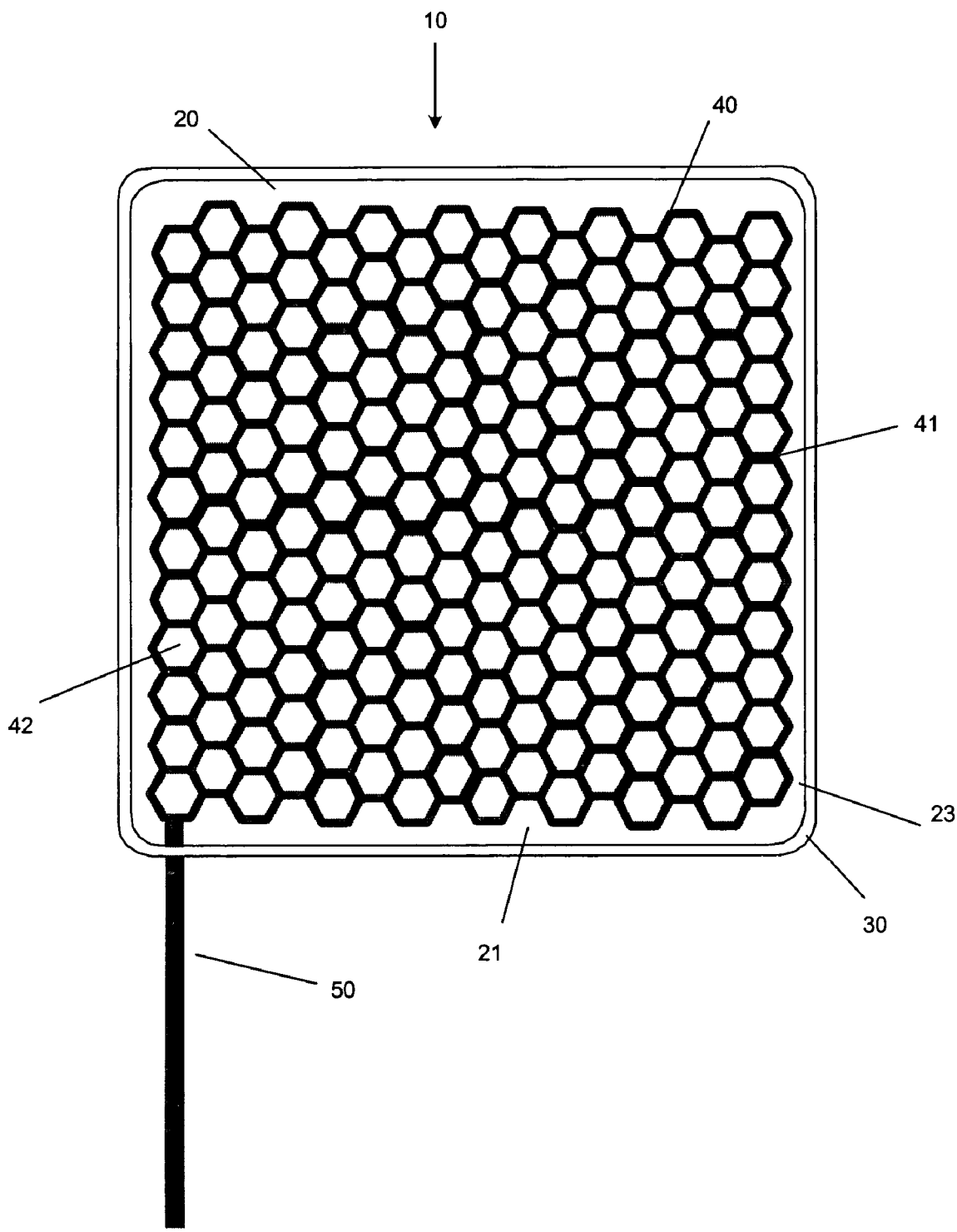
FIG. 2 is a schematic diagram of the electrode arrangement according to the first embodiment of the present invention.

FIG. 2 is a schematic plan view of the electrode arrangement 10 showing the first surface 21 of the printed circuit board 20. The electrically conductive tracks 41 are arranged in the form of a honeycomb mesh structure. The electrically conductive gel 42 is spread over the first surface 21 of the printed circuit board 20 into the gaps between the electrically conductive tracks 41 thereby forming further electrically conductive connections between the electrically conductive tracks 41, enhancing electrical conductivity across the surface of the electrode and providing a electrically conductive path between the electrode 40 and the skin. The sealing gel 30 is placed on a nonconductive portion 23 at the edges of the first surface 21 of the printed circuit board 20 in the form of a strip around the periphery of the printed circuit board 20. The printed circuit board 20 is fabricated from a flexible polyester film. The combination of the honeycomb mesh pattern of electrically conductive tracks 41 and electrically conductive gel 42, with the polyester film printed circuit board provides an electrode arrangement which is flexible in a direction perpendicular to the plane of the electrode arrangement. This flexibility allows the electrodes 40 to make good electrical contact with the uneven or curvaceous surface of the skin when placed on the skin 60 with the first surface 21 of the printed circuit board 20 placed facing the skin 60. Furthermore this arrangement helps to eliminate hot spots resulting from uneven electrical-skin contact.

It should be appreciated that the gaps between the electrically conductive tracks 41 need only be sufficiently large to permit flexion of the printed circuit board.

Figure 3:
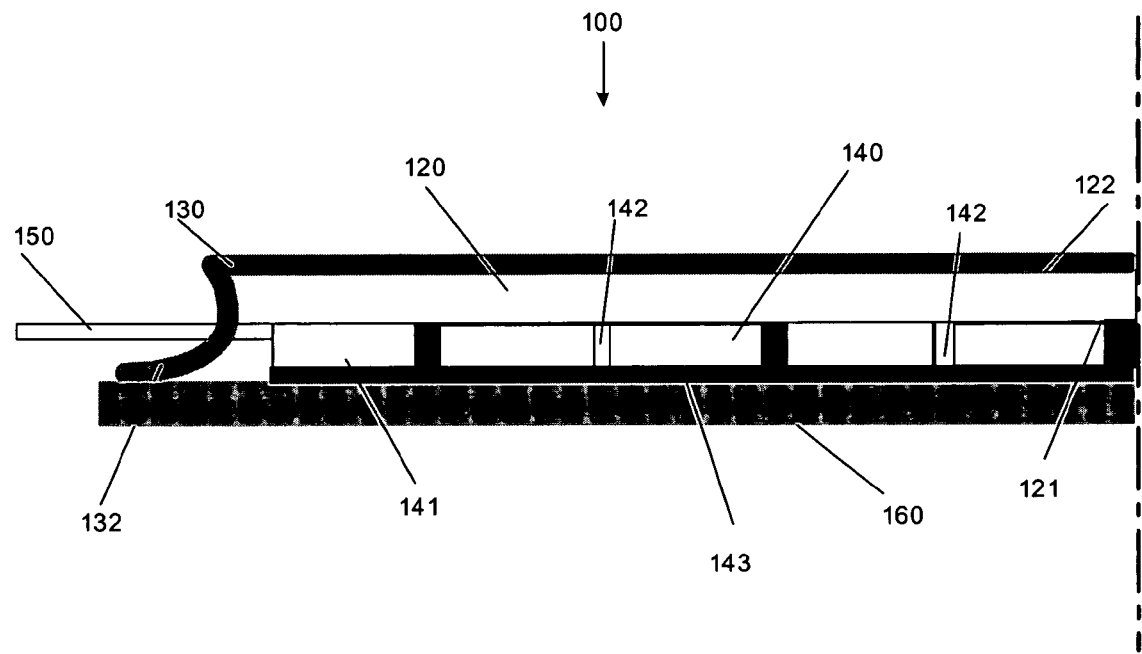
FIG. 3 is a partial cross sectional view of an electrode arrangement according to a second embodiment of the present invention.

FIG. 3 is a partial cross sectional view of an electrode arrangement 100 placed on the skin 160 of a patient according to a second embodiment of the invention comprising a flexible electrically non-conducting printed circuit board 120 having a first surface 121 and a second surface 122 opposed to the first surface 121, a waterproof sealing pad 130 to prevent ingress of moisture to any exposed conductive elements of the electrode arrangement, an electrode 140 for applying electrical signals to the skin when placed on the skin, and a connector 150 for supplying electrical signals to the electrode 140. The electrode 140 comprises electrically conductive elements 141 and flexible electrically conductive links 142. Electrically conductive gel 143 is applied to the electrode 140 to provide an electrically conductive path between the electrode 140 and the skin. The sealing pad 130 is placed over the second surface 122 of the printed circuit board 120. The outer edges 132 on one surface of the sealing pad 130 have adhesive properties and the sealing pad is positioned such that the edges 132 of the sealing pad extend beyond the edges of the printed circuit board 120 in all directions and adhere the printed circuit board to the skin. The sealing pad 130 may be any type of waterproof adhesive material of the kind generally used in medicine.

Figure 4:
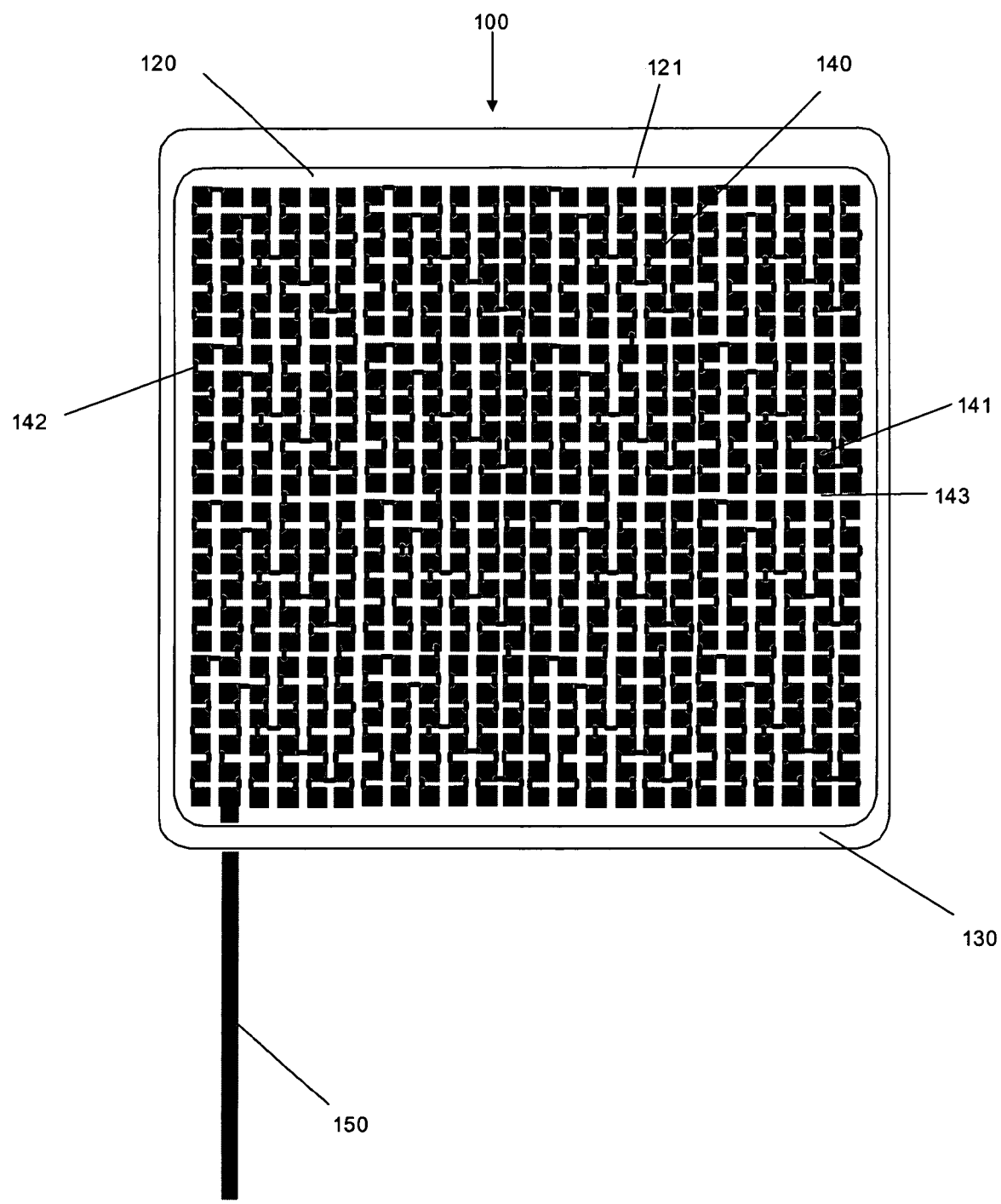
FIG. 4 is a schematic diagram of the electrode arrangement according to the second embodiment of the present invention.

FIG. 4 is a schematic plan view of the electrode arrangement 100 according to the second embodiment of the invention showing the first surface 121 of the printed circuit board 120. The electrically conductive elements 141 are square shaped and are etched out of a layer of conductive material such as gold plated copper on the first surface 121 of the printed circuit board 120 in a matrix. Flexible electrically conductive links 142 are disposed between some of the electrically conductive elements 141 to form a bi-dimensional electrically conductive path across a portion of the first surface 121 of the printed circuit board 120. The printed circuit board 120 is fabricated from a polyester film. The combination of the matrix of electrically conductive elements 141 and the flexible electrically conductive links 143, with the polyester film printed circuit board 120 provides an electrode arrangement which is flexible in a direction perpendicular to the plane of the electrode arrangement. Electrically conductive gel 143 is applied to the electrode 140 to provide an electrically conductive path between the electrode and the skin. Such an arrangement provides an electrode arrangement which makes good contact with uneven surfaces such as the skin.

Although in this embodiment a polyester film is used as the printed circuit board, in alternative embodiments any flexible PCB material may be used.

Figure 5:
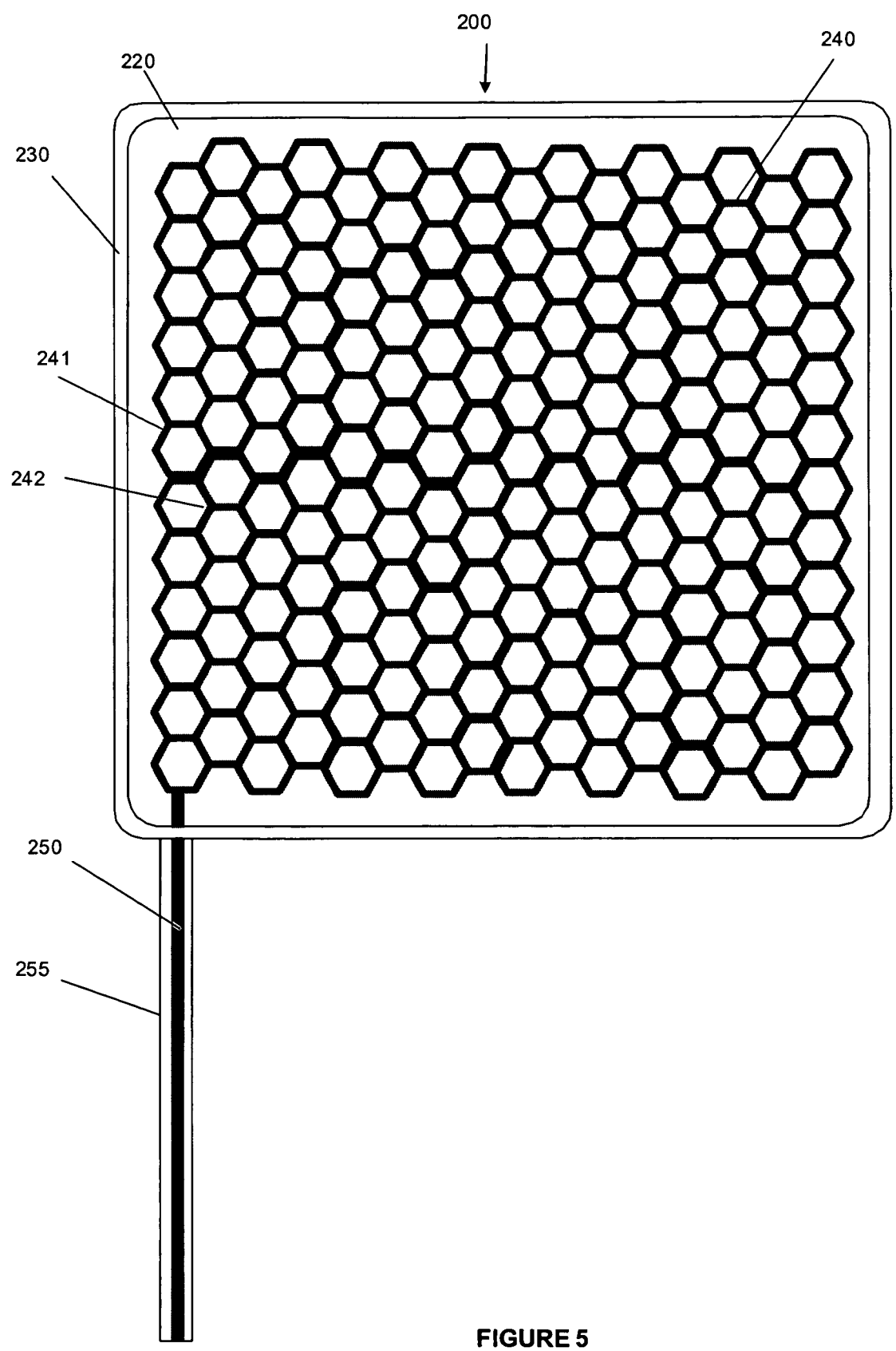
FIG. 5 is a schematic diagram of an electrode arrangement according to a third embodiment of the present invention.

FIG. 5 is a schematic plan view of an electrode arrangement 200 according to a third embodiment of the present invention. The electrode arrangement 200 comprises a flexible electrically non-conducting printed circuit board 220 with an extended portion 255, an electrode 240 comprising a honeycomb mesh pattern of electrically conductive tracks 241 and electrically conductive gel 242. Waterproof sealing gel 230 is placed around the edges of the printed circuit board to provide a seal between the electrode arrangement and skin preventing the ingress of moisture. The extended portion 255 of the printed circuit board 220 carries a flexible electrical connector 250 which when connected to an electrical current generator can carry current to the electrode 240. The portion of the flexible electrical connector on the extended portion is electrically insulated by an insulating layer on top of the flexible electrical connector 250. The extended portion provides a flat lead to the electrode which will not indent the skin of a patient or cause discomfort and will not appear as a raised region or bulge when covered with a bandage or other type of medical dressing.

Figure 6:
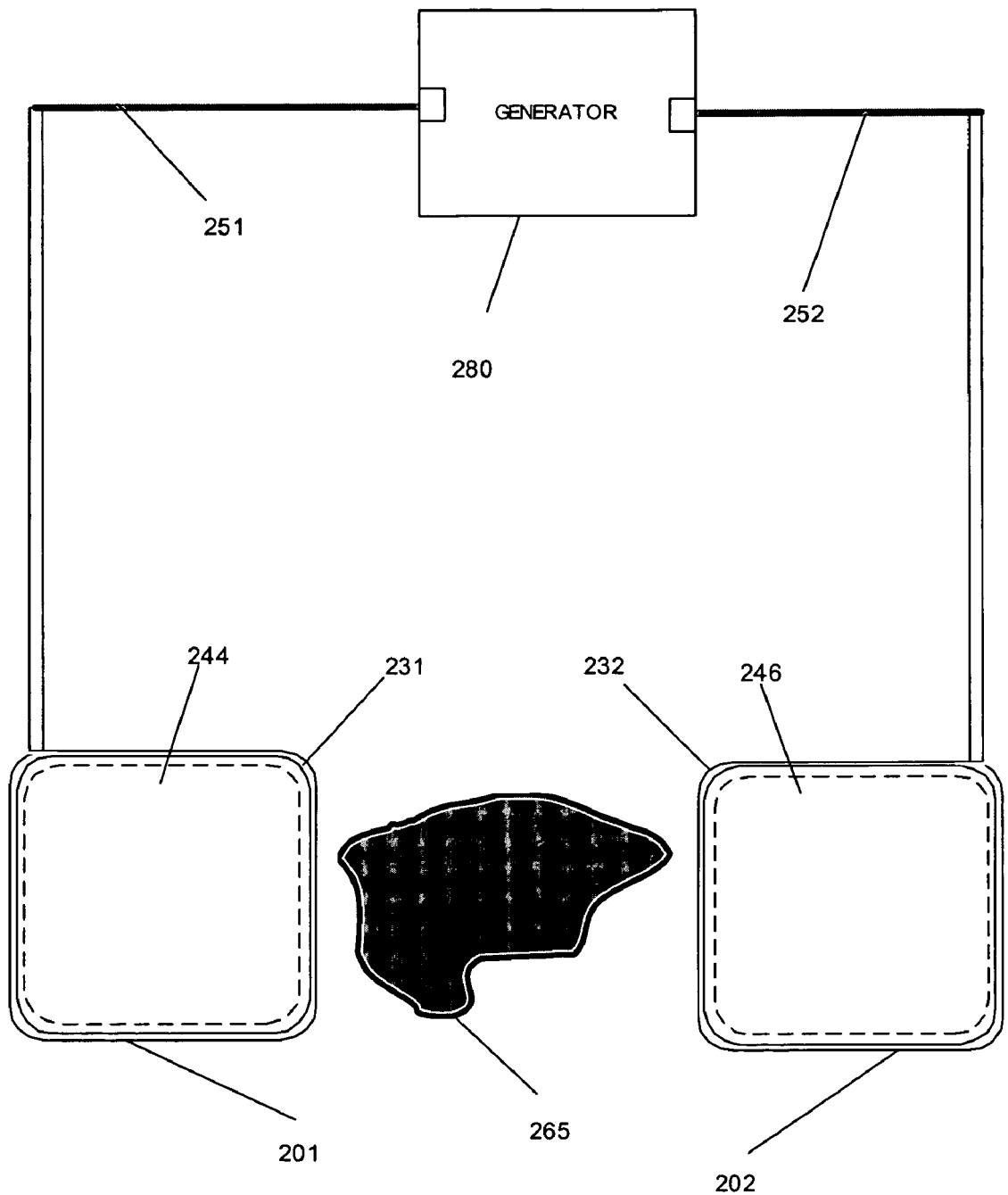
FIG. 6 is a schematic diagram of an area of treatment showing electrode arrangements of FIG. 5 placed around a wound.

FIG. 6 is a schematic plan view of an area of treatment in which electrode arrangements according to the third embodiment of the invention are placed around a wound 265 of a human patient. Electrode arrangements 201 and 202 are placed on the skin on opposite sides of the wound 265 with the first surface of the printed circuit board of each electrode arrangement arranged to face the skin. The edges of the printed circuit boards of 201 and 202 on which adhesive sealing gel 231 and 232, respectively, is applied, are pressed against the skin in order to adhere the electrode arrangement to the surface of the skin. This arrangement creates a seal preventing the ingress of moisture to any exposed conductive components of the electrode arrangements. The electrode arrangements 201 and 202 are connected to an electrical generator circuit 280 via connectors 251 and 252, respectively, which are provided on the extended portions of printed circuit boards 201 and 202 respectively. Electrical signals generated by the electrical generator 280 pass through the connectors 251 and 252 to electrodes 244 and 246, respectively (shown as dotted areas). From the electrodes 244 and 246 pressed against the skin of the patient, the electrical signals are administered to the skin of the patient around the wound. Such an arrangement promotes wound healing by passing electrical current between the electrodes through regenerative tissues under the wound.

Figure 7:
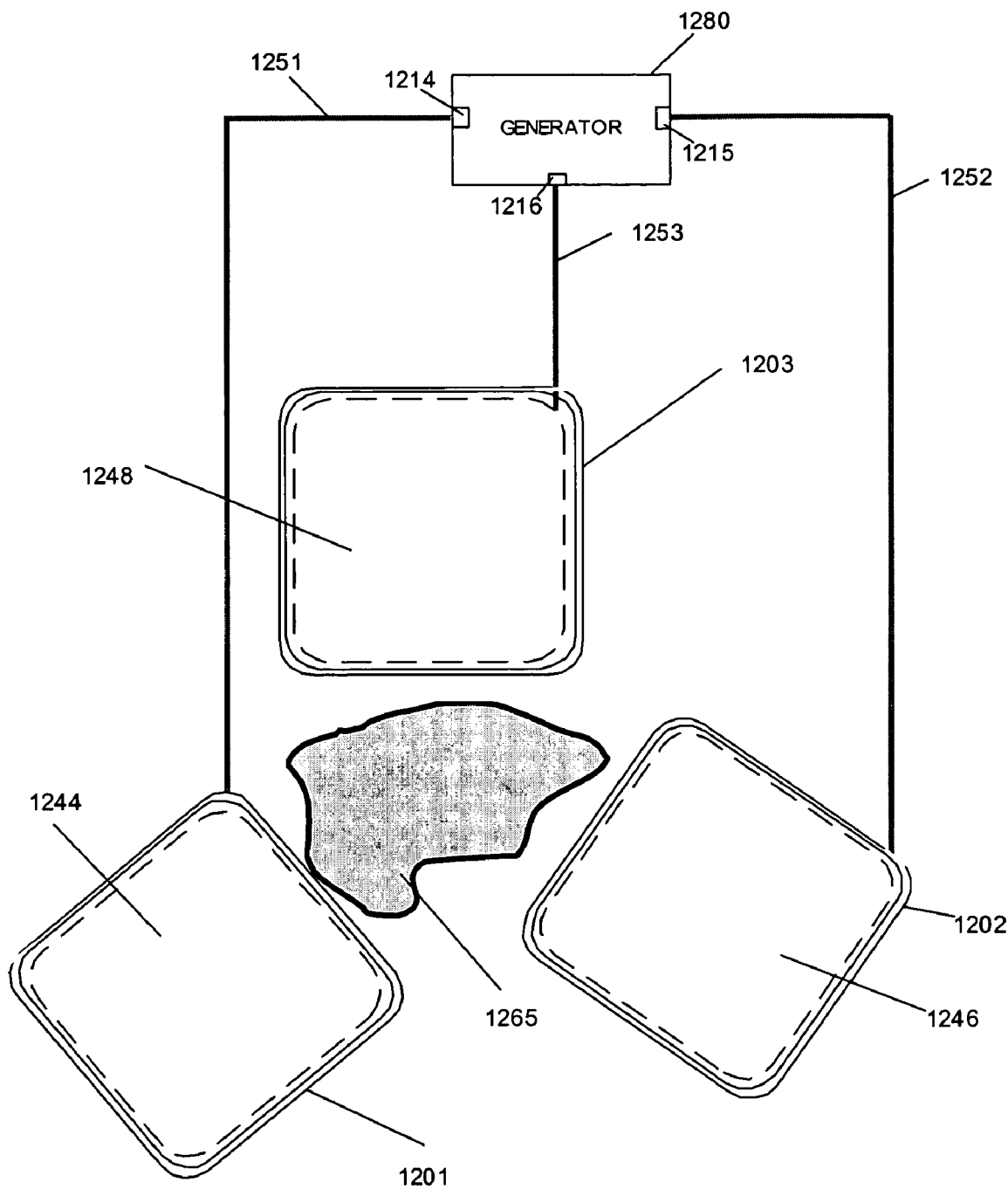
FIG. 7 is a schematic diagram of an area of treatment showing electrode arrangements of FIGS. 1 and 2 disposed around a wound.

FIG. 7 is a schematic view of an area of treatment in which electrode arrangements according to the first embodiment of the invention are placed around a wound. Electrode arrangements 1201, 1202 and 1203 are arranged around a wound 1265. The first surface of the printed circuit board of the electrode arrangements are arranged to face the skin of the patient. The outer edges of the printed circuit boards of electrode arrangements 1201, 1202 and 1203 on which adhesive gel is applied is pressed against the skin to seal the electrode arrangement to the skin and prevent the ingress of moisture to any exposed conductive components. Connecting leads 1251, 1252 and 1253 are connected between an electrical generator circuit 1280 and to electrode arrangements 1201, 1202 and 1203, respectively. Connector 1251 supplies electrical signals from the electrode output port 1214 of generator 1280 to electrode 1244, electrical connector 1252 supplies signals from the electrode output port 1215 of generator 1280 to electrode 1246 and electrical connector 1253 supplies signals from the electrode output port 1216 of generator 1280 to electrode 1248. Electrical current can therefore be applied between different electrodes, thereby passing through different paths under the wound. For example, electrical current may be applied to pass from electrode 1244 to electrode 1248 or from electrode 1244 to electrode 1246. Furthermore, the direction of the current flow may be reversed so that current flows from electrode 1248 to electrode 1244, or from electrode 1246 to electrode 1244 Alternatively, electrical current may be applied to pass from electrode 1248 to electrodes 1244 and 1246 simultaneously, or alternatively, to pass from electrodes 1244 and 1246 to electrode 1248. It may be appreciated that it is possible to apply the current to flow between many combinations of different electrodes.

Although, in this embodiment three electrodes are used, any number of electrodes may be placed around the wound to provide finer angular steps between electrode positions and resulting in more complex current profile patterns across the area of treatment if required. Current may be applied to flow between different electrodes simultaneously or in a sequence depending on the treatment required. Furthermore, the electrical generator 1280 may be programmed to provide a predetermined sequence of current profiles through different paths across the treatment area.

Figure 8:
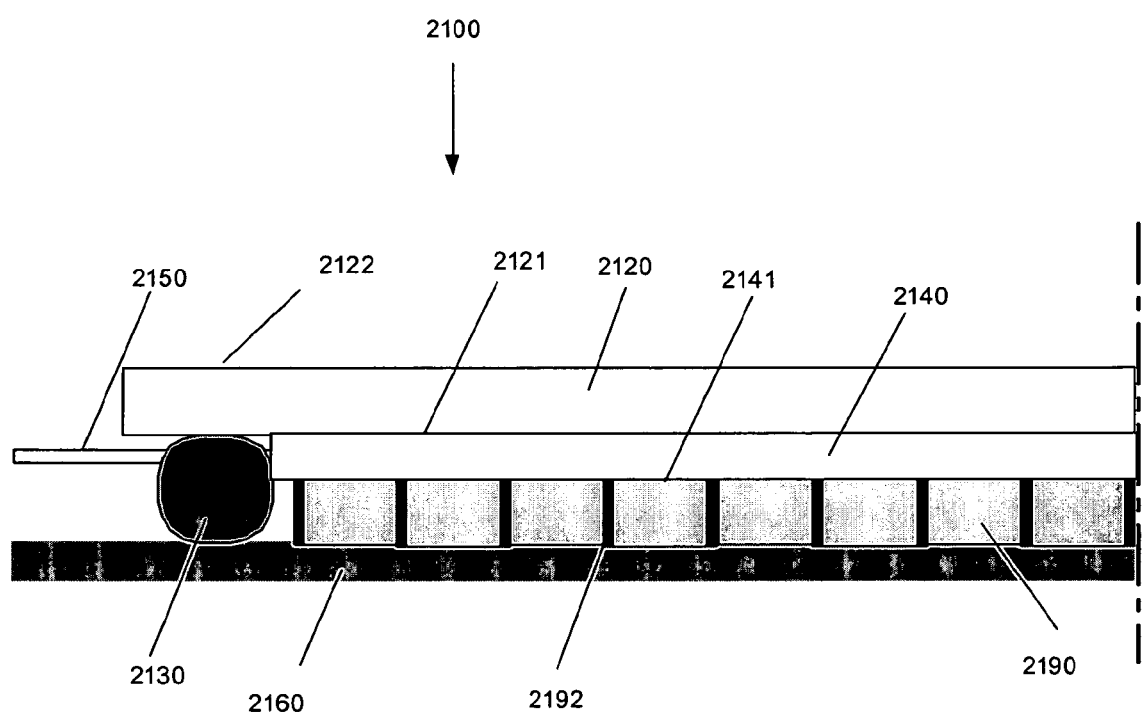
FIG. 8 is a partial cross sectional diagram of an electrode arrangement according to a fourth embodiment of the invention.

FIG. 8 is a partial cross-sectional diagram of an electrode arrangement 2100 according to a fourth embodiment on the invention disposed on the surface of the skin 2160 of a patient. The electrode arrangement comprises a flexible electrically non-conductive substrate 2120 having a first surface 2121 facing towards the skin when the electrode arrangement is placed on the skin and a second surface 2122 opposed to the first surface, electrically non-conductive sealing gel 2130, an electrode 2140 for applying electrical signals to the skin 2160, and an electrically conductive lead 2150 for supplying electrical signals to the electrode 2140. The electrode 2140 has a first surface 2141 facing towards the skin when the electrode arrangement is placed on the skin. A plurality of interconnected electrically insulating rubber elements 2192 are disposed on the first surface 2141 of the electrode 2140. The rubber elements are arranged in a honeycomb mesh structure across the first surface 2141 of the electrode 2140 and each rubber element extends from the first surface 2141 of the electrode 2140 towards the surface of the skin 2160 when the electrode arrangement is placed on the skin. Portions of gel with high electrical resistance 2190 are disposed on the first surface 2141 of the electrode 2140 between the electrically insulating rubber elements 2192. Such an arrangement renders any resistance of the skin and the electrode negligible in comparison to the resistance of the gel. Consequently, any differences in resistances of the electrode and the skin across the surface of the electrode will be rendered imperceptible. The result will be a more even distribution of current across the surface of the electrode.

Although in this embodiment, portions of electrically insulating rubber are used it may be understood that any electrically insulating material providing flexibility may be used. Furthermore, although gel of high electrical resistance is used in this embodiment, in alternative embodiments any material of high electrical resistance may be used.

Although in this embodiment the portions of electrically insulating rubber are arranged in the form of a honeycomb mesh structure, in alternative embodiments of the invention, the portions of electrically insulating rubber may be arranged in any mesh or grid structure preventing a path of electrically conductivity to be created through the mesh structure.

Figure 9:
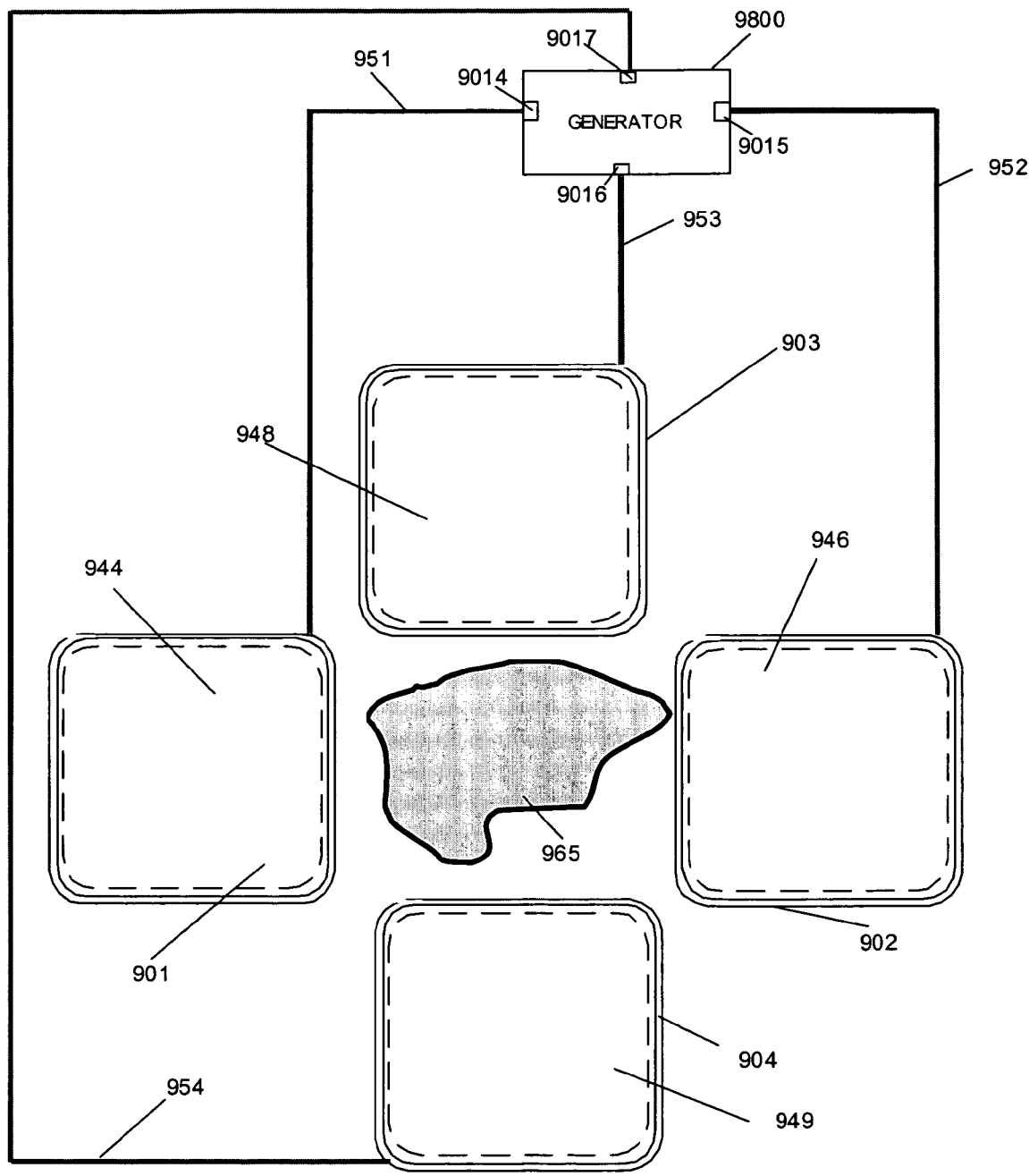
FIG. 9 is a schematic diagram of an area of treatment showing four electrode arrangements of FIG. 8 disposed around a wound.

FIG. 9 is a schematic view of an area of treatment in which four electrode arrangements according to the fourth embodiment of the invention are placed around a wound. Electrode arrangements 901, 902, 903 and 904 are arranged around a wound 965. The first surface of the printed circuit board of the electrode arrangements are arranged to face the skin of the patient. The outer edges of the printed circuit boards of electrode arrangements 901, 902, 903 and 904, on which adhesive gel is applied, is pressed against the skin to seal the electrode arrangement to the skin and to prevent the ingress of moisture to any exposed component parts. Connecting leads 951, 952, 953 and 954 are connected between an electrical generator circuit 9800 capable of generating a bi-directional constant current, and electrode arrangements 901, 902, 903 and 904, respectively. Connector 951 supplies electrical signals from the electrode output port 9014 of generator 9800 to electrode 944, electrical connector 952 supplies signals from the electrode output port 9015 of generator 9800 to electrode 946, electrical connector 953 supplies signals from the electrode output port 9016 of generator 9800 to electrode 948, and electrical connector 954 supplies electrical signals from the electrode output port 9017 of generator 9800 to electrode 949. Electrical current can therefore be applied to pass under the wound between different electrodes. A maximum current limit can be set on the electrical current generated by the electrical generator 9800 for each pair of electrodes. Any combination of electrodes may be used thereby forming a matrix of current paths under the wound and ensuring a more even distribution of current. For example electrical current may be applied to pass from electrode 948 to electrode 949 and from electrode 946 to electrode 944. The direction of the current passing between one or both of these pairs of electrodes may be reversed. Alternatively, electrical current may be applied to pass from electrode 948 to electrode 946 and from electrode 944 to electrode 949. Again, the direction of the current passing between one or both of these pairs of electrodes may be reversed. It may be appreciated that it is possible to apply current to flow between many combinations of different electrodes. The current may be applied to flow between different electrodes simultaneously or sequentially.

In alternative embodiments of the invention the current may be applied by feeding each electrode current though a resistor having a resistance substantially greater than the resistance of the skin and the electrode. Such an arrangement renders any differences in resistances of the electrode and the skin at different points across the surface of the electrode insignificant and thus has the effect of providing a more even distribution of current.

Figure 10:
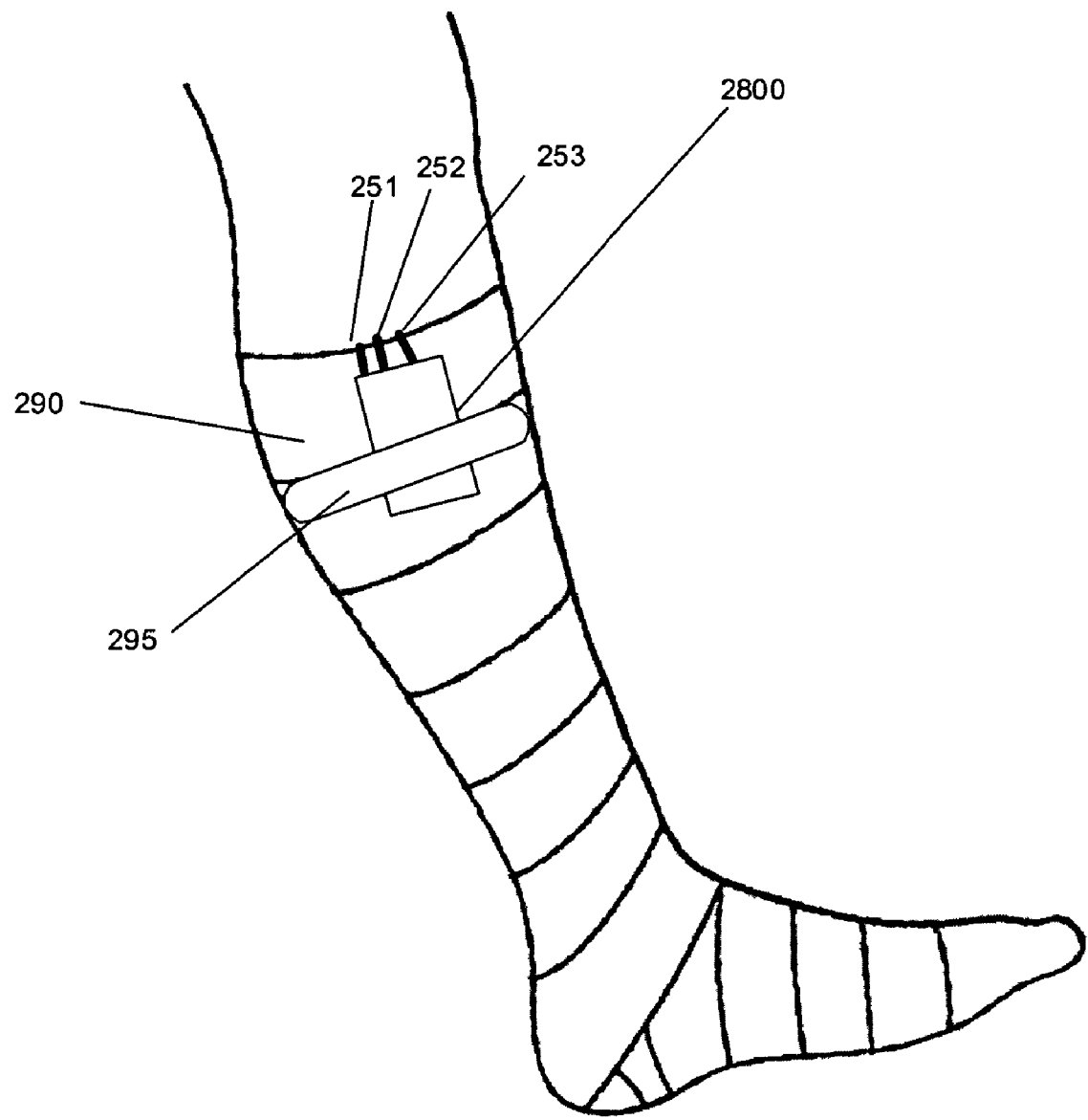
FIG. 10 is a schematic diagram of an area of treatment according to an embodiment of the invention.

FIG. 10 schematically illustrates the area of treatment of FIG. 7 covered by a bandage 290. Electrical generator 2800 is located outside the bandage 290 and attached to the leg by adhesive medical tape 295. Electrical interface between the electrical generator 2800 and electrodes is made through connectors 251, 252 and 253.

Figure 11A:
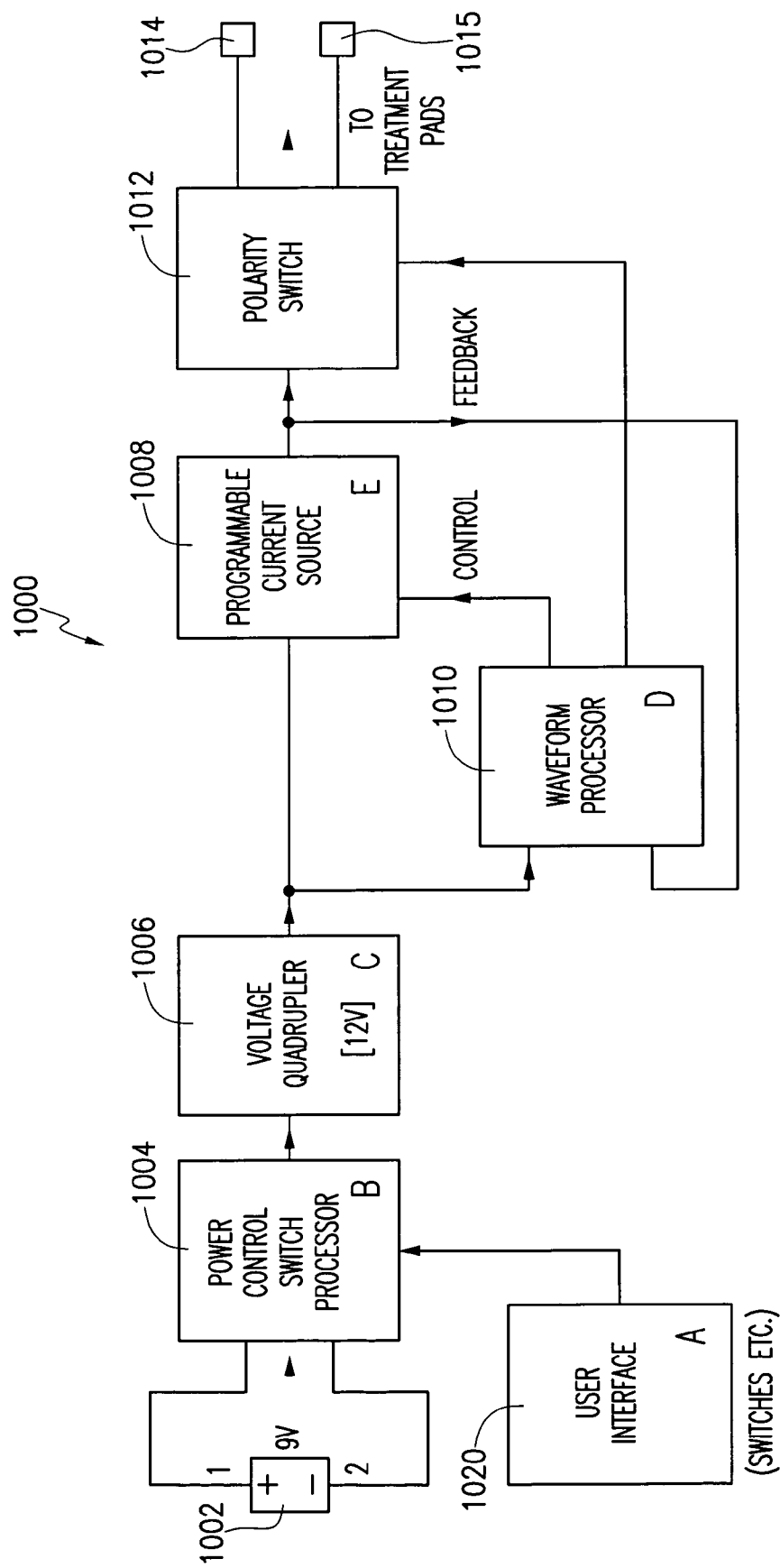
FIG. 11A is a schematic diagram of a device for generating electrical current according to an embodiment of the invention.

A schematic diagram of an electrical generator circuit according to an embodiment of the invention is shown in FIG. 11A. The electrical generator circuit 1000 comprises a battery 1002, a power control processor 1004, a voltage multiplier 1006, a programmable current source 1008, a waveform processor 1010, a polarity switch 1012, a user interface 1020, electrode ports 1014 and 1015. The device 1000 can be connected to electrode arrangements through electrode ports 1014 and 1015.

Power control processor 1004 can activate the generation of current waveforms through user interface 1020 or automatically at predetermined times. Battery 1002 is a lithium coin cell type and runs the power control processor 1004 in low power mode. When current is required, power is supplied to the voltage multiplier 1006.

In this embodiment voltage multiplier 1006 is a dc-dc converter and multiplies the input voltage using a charge pump circuit. The charge pump circuit is power limited thereby providing a "fail-safe" operation. The voltage multiplier 1006 supplies a pumped voltage to the waveform processor 1010 and the programmable current source 1008.

Waveform processor 1010 controls the programmable current source 1008 and controls the polarity switch 1012. The programmable current source 1008 includes a feedback loop with the waveform processor 1010. Waveform processor 1010 monitors the output voltage between electrodes connected to electrode ports 1014 and 1015.

Programmable current source 1008 receives control signals from the waveform processor 1010 and converts them into an appropriate output current waveform.

Polarity switch 1012 receives a control signal from the waveform processor 1010 and a current signal from programmable current source 1008. The polarity switch 1012 supplies the generated current waveform to electrode ports 1014 and 1015. In this embodiment polarity switch 1012 is a double pole change over switch utilising solid state analogue switches to switch polarity of the outputs. The direction of the current waveform applied between electrode ports 1014 and 1015 can thereby be switched.

The electrical generator circuit 1000 can be programmed to generate current waveforms with different parameters and can control the frequency and duration of application of current waveforms. This allows treatment of wounds to be tailored to individual patients needs. Furthermore, the battery allows electrical signals to be generated for over 35 hours. The system is therefore suitable for long-term treatments.

Figure 11B:
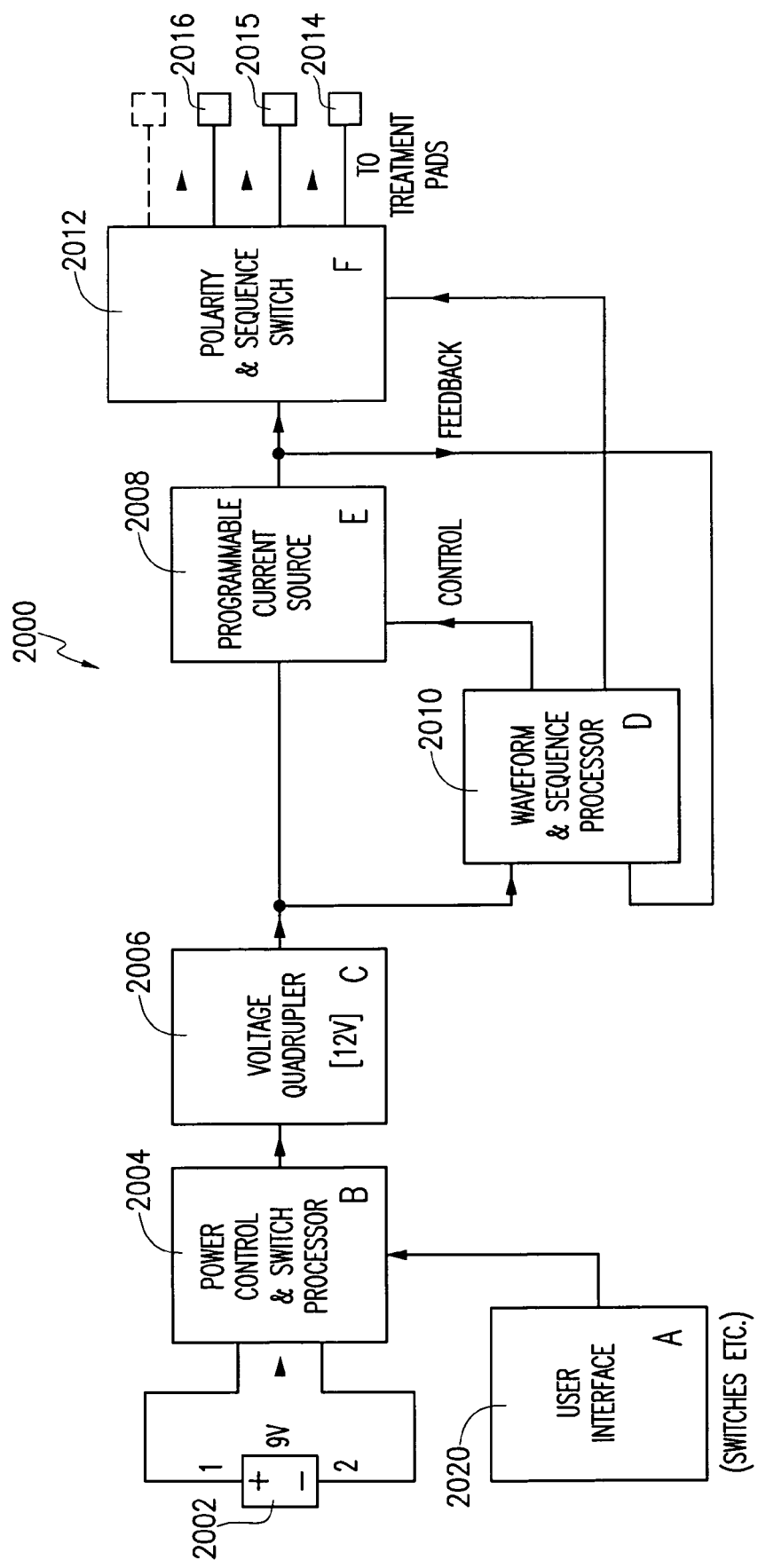
FIG. 11B is a schematic diagram of a device for generating electrical current according to an alternative embodiment of the invention.

A further embodiment of a device for generating electrical waveforms is shown in FIG. 11B. In this embodiment the device 2000 comprises a polarity and connection sequence switch 2012, a waveform and sequence processor 2010, a voltage multiplier 2006, a programmable current source 2008, a power control processor 2004, a battery 2002 and a plurality of electrode ports 2014, 2015 and 2016. The device 2000 can be connected to electrode arrangements through electrode ports 2014, 2015 and 2016.

Power control processor 2004 operates in a similar fashion to power control processor 1004 of the previous embodiment.

The waveform and sequence processor 2010 controls the programmable current source 2008 and the polarity and connection sequence switch 2012. Programmable current source 2008 receives control signals from the waveform processor 2010 and converts them into an appropriate output current waveform.

Polarity and connection switch 2012 receives a control signal from the waveform and sequence processor 2010 and a current waveform signal from programmable current source 2008. The polarity and connector switch supplies the current waveform to a pair of appropriate electrode ports 2014 and 2015, 2014 and 2016, or 2015 and 2016 based on the control signals received from the waveform and sequence processor 2010. The current waveforms may also be applied to flow from two ports to one port or from one port to two ports simultaneously. The polarity and connection switch 2012 uses solid state analogue switches to switch the polarity of the current waveform and connect different combinations of electrode ports to the programmable current source. This arrangement allows the direction of the current to be switched and different combinations of electrode ports to be used.

Although in this embodiment the generator has only three electrode ports, any number of ports may be used.

Although in the embodiments of FIGS. 11a and 11b, a cell battery, a power control processor and a voltage multiplier are used to power the circuit, in alternative embodiments a single battery cell of higher voltage may be used to replace the battery, the power control processor and the voltage multiplier.

Figure 12:
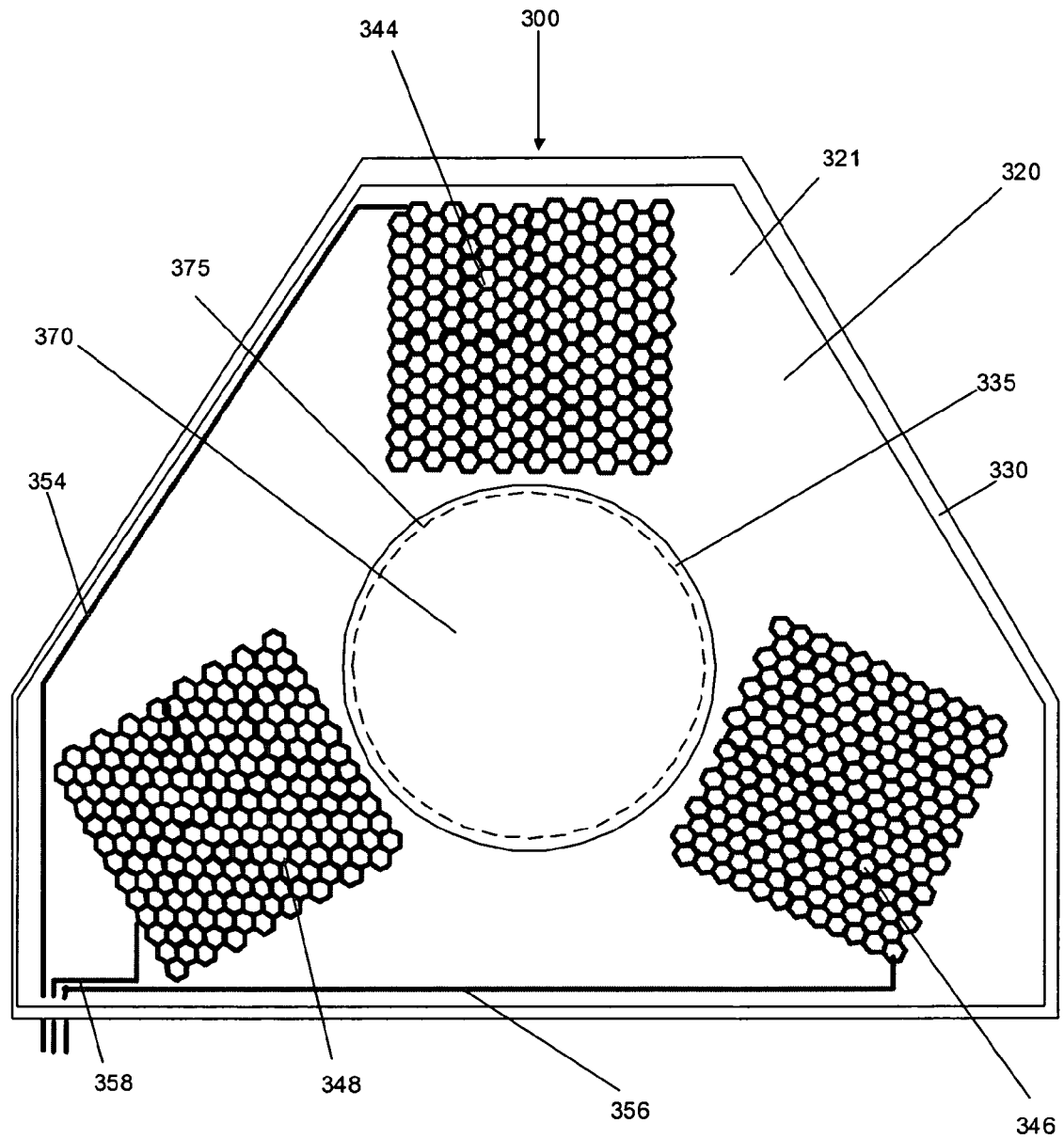
FIG. 12 is a schematic diagram of an electrode arrangement according to a fifth embodiment of the invention.

FIG. 12 is a schematic view of an electrode arrangement 300 according to a fifth embodiment of the invention. In this embodiment the electrodes are provided on one common printed circuit board. The electrode arrangement 300 comprises a common printed circuit board 320, three electrodes 344, 346 and 348 comprising a mesh structure of conductive tracks and conductive gel on a first surface 321 of the printed circuit board 320. Perforations 375 allow a portion of the substrate to be removed to create an aperture 370 located in the central region of the printed circuit board 320. The electrodes 344, 346 and 348 are arranged around the aperture 370. Each electrode is electrically isolated from another electrode. Connectors 354, 356, and 358 provide electrical signals to the electrodes 344, 346, and 348, respectively, when connected to an electrical generator. A strip of waterproof, electrically non-conductive sealing gel 330 is disposed around the edges of the printed circuit board 320 to prevent the ingress of moisture into the electrode arrangement 300. An annulus of electrically non-conducting gel 335 is disposed around the edges of the aperture 370. This arrangement has the advantage that the electrodes are provided on a common substrate. As well as being practical, since the electrodes are fixed on the substrate the relative position between the electrodes will not change during an electrotherapy procedure.

Although in this embodiment the substrate is provided with three electrodes, it may be appreciated that any number of electrodes may be provided on the surface to provide finer angular steps of electrodes around a wound.

Although in this embodiment electrically non-conductive sealing gel is placed around the edges of the aperture 370 and the edges of the printed circuit board, in alternative embodiments the sealing gel may be placed around each electrode provided on the substrate.

In alternative embodiments, the printed circuit board may already be provided with an aperture.

Figure 13:
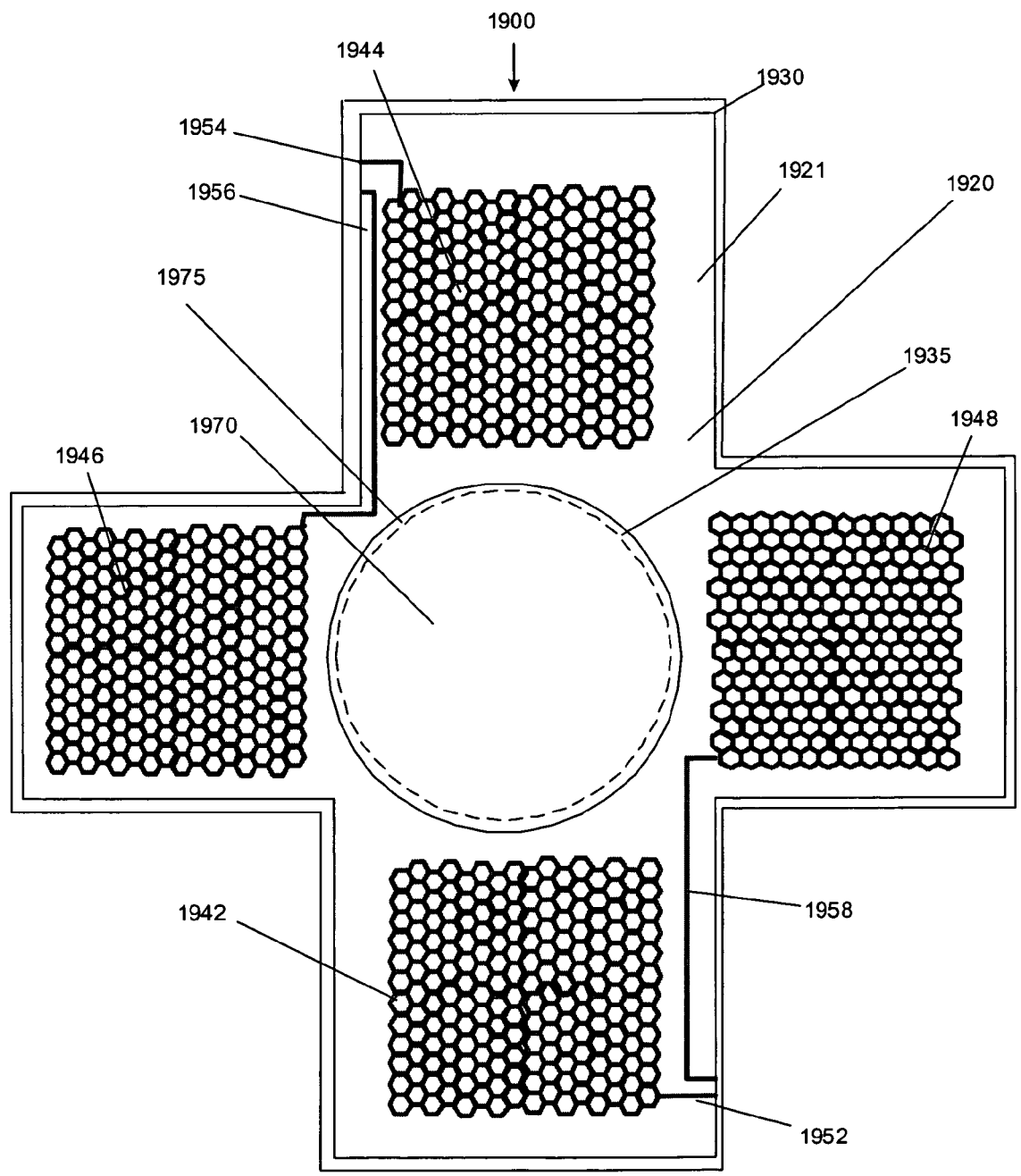
FIG. 13 is a schematic diagram of an electrode arrangement according to a sixth embodiment of the invention.

FIG. 13 is a schematic diagram of an electrode arrangement 1900 according to a sixth embodiment of the invention. In this embodiment four electrodes are provided on one common printed circuit board. The electrode arrangement 1900 comprises a common printed circuit board 1920, four electrodes 1942, 1944, 1946 and 1948 comprising a mesh structure of conductive tracks and conductive gel on a first surface 1921 of the printed circuit board 1920. Perforations 1975 allow a portion of the substrate to be removed to create an aperture 1970 located in the central region of the printed circuit board 1920. The electrodes 1942, 1944, 1946 and 1948 are arranged around the aperture 1970. Each electrode is electrically isolated from another electrodes. Connectors 1952, 1954, 1956 and 1958 provide electrical signals to the electrodes 1942, 1944, 1946 and 1948 respectively, when connected to an electrical generator. A strip of waterproof, electrically, non-conductive sealing gel 1930 is disposed around the edges of the printed circuit board 1920 to prevent the ingress of moisture into the electrode arrangement 1900. An annulus of electrically non-conducting gel 1935 is disposed around the edges of the aperture 1970. This arrangement has the advantage that the electrodes are provided on a common substrate.

Although in this embodiment the substrate is provided with four electrodes, it may be appreciated that any number of electrodes may be provided on the surface to provide finer angular steps of electrodes around a wound.

Figure 14:
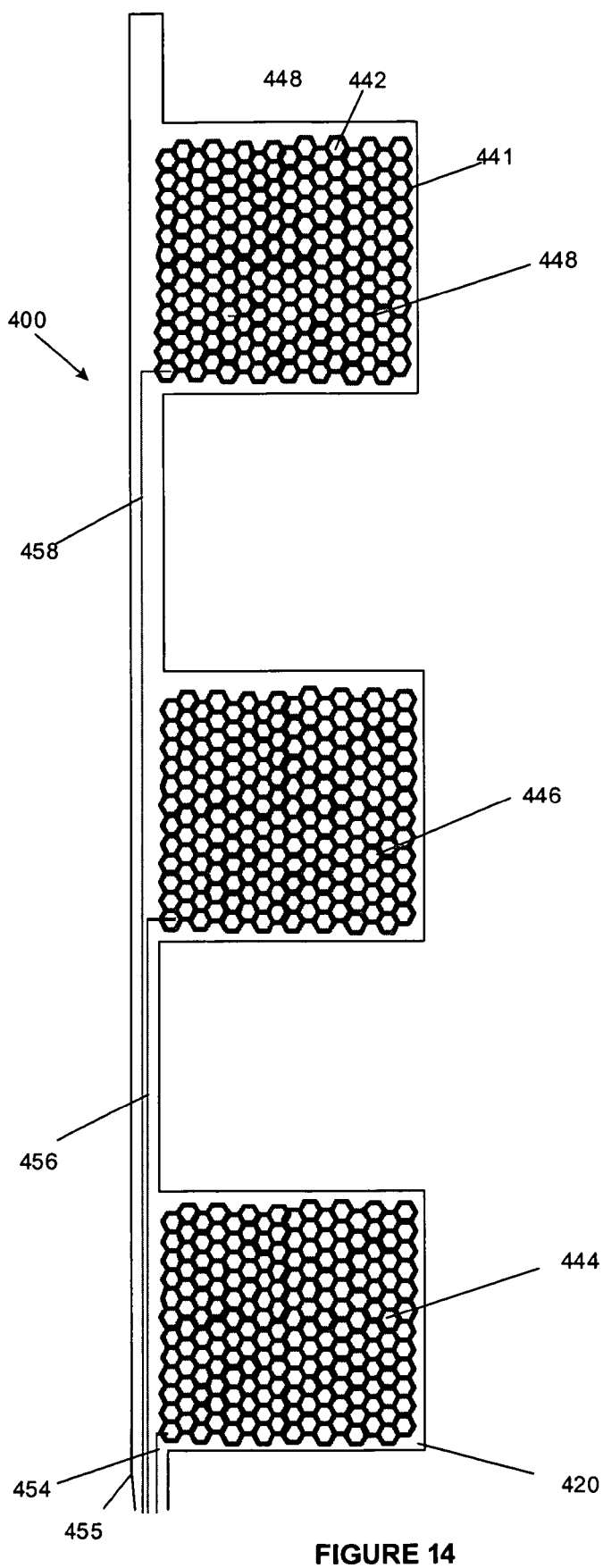
FIG. 14 is a schematic view of an electrode arrangement according to a seventh embodiment of the invention, placed on an area of treatment.

FIG. 14 is a schematic view of an electrode arrangement 400 according to a seventh embodiment of the invention. The electrode arrangement comprises a substrate 420, three electrodes 444, 446 and 448 provided on to first surface 421 of the substrate 420. Each of the electrodes comprises electrically conductive tracks 441 and conductive gel 442. The substrate has an extended portion 455 carrying electrical connectors 454, 456 and 458. Electrical connectors 454, 456 and 458 are electrically isolated from one another. Electrical connector 454 is connected to electrode 444, electrical connector 456 is connected to electrode 446 and electrical connector 458 is electrically connected to electrode 448. The flexible substrate allows the electrodes 444, 446 and 448 to be bent into a shape that can be placed around a wound.

Again, although in this embodiment three electrodes are provided on the substrate any number of electrodes may be provided on the substrate.

Figure 15:
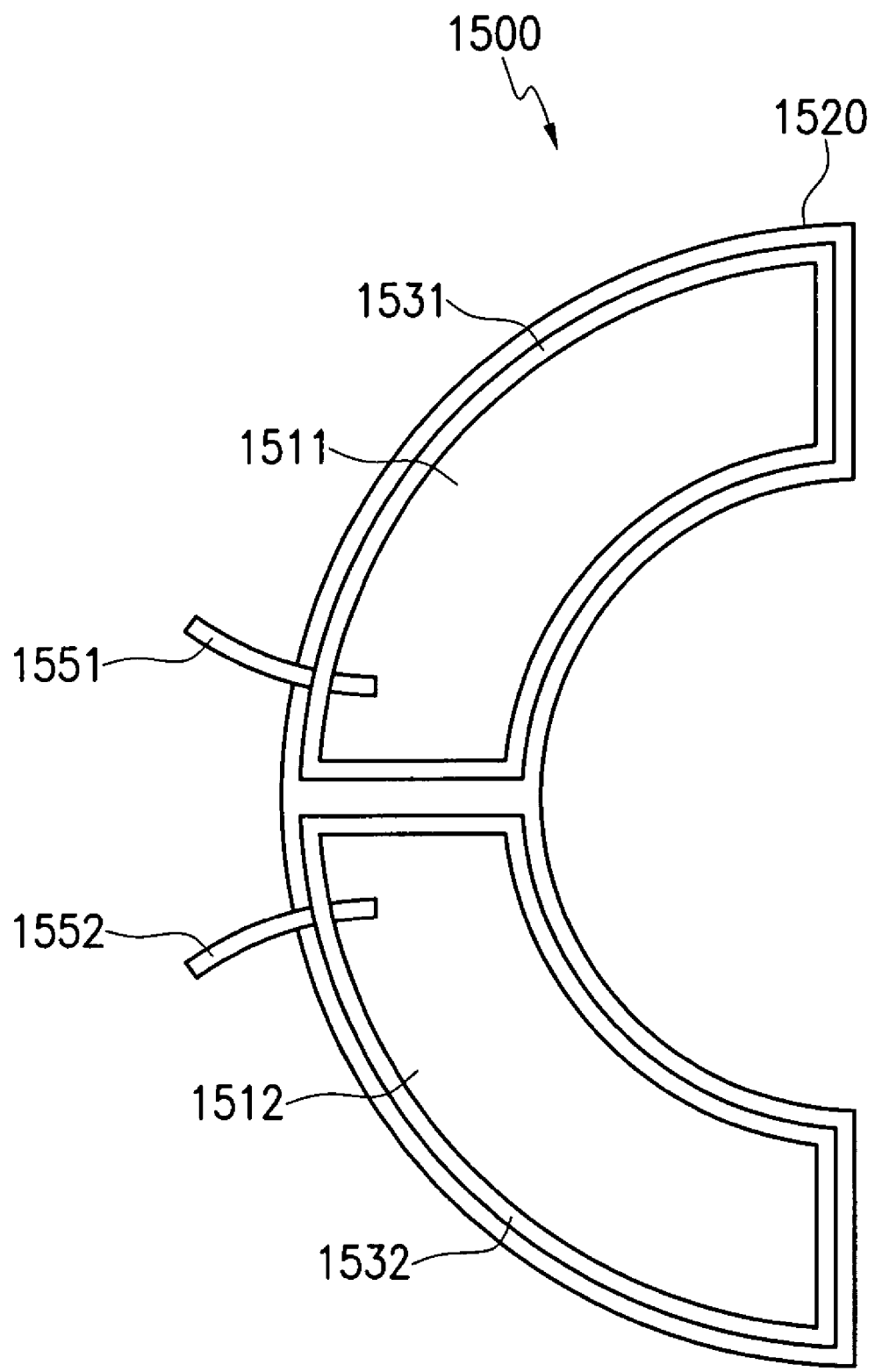
FIG. 15 is a schematic view of an electrode arrangement according to an eighth embodiment of the invention.

FIG. 15 is a schematic plan view of an electrode arrangement 1500 according to an eighth embodiment of the invention. The electrode arrangement 1500 comprises a substrate 1520 formed in a part annular shape, and having a first surface and a second surface opposed to the first surface. Two electrodes 1511 and 1512 are provided on the first surface of the substrate 1520. The electrodes 1511 and 1512 are each formed in a part annular shape and comprise electrically conductive tracks and electrically conductive gel. The electrodes are electrically insulated from one another. Connectors 1551 and 1552 provide electrode signals to the electrodes 1511 and 1512, respectively when connected to an electrical generator. A strip of waterproof, electrically non-conductive sealing gel 1531 is disposed around the edges of the electrode 1511 and over electrical connector 1551 to prevent ingress of moisture to the electrically conductive parts of the electrode 1511 and the electrical connector 1551. A strip of waterproof, electrically non-conductive sealing gel 1532 is disposed around the edges of the electrode 1512 and over electrical connector 1552 to prevent ingress of moisture to the electrically conductive parts of the electrode 1512 and the electrical connector 1552. This arrangement has the advantage that the electrode arrangement may be placed close to the edge of the wound.

While in this embodiment the substrate has a part annular shape, in alternative embodiments of the invention, the substrate may have a crescent shape. It should also be readily appreciated that while FIG. 15 shows a part annular substrate covering an angle of around 180 degrees, in alternative embodiments the part annular substrate may cover any angle from 0 to 360 degrees.

Although in this embodiment each electrode arrangement has two electrodes, in alternative embodiments each electrode arrangement may have one electrode or any number of electrodes.

Furthermore, although adhesive sealing gel is disposed around each electrode of the electrode arrangement in the above embodiment. In alternative embodiments the conductive gel may be disposed around the edges of the electrode arrangement and over each connector.

Figure 16:
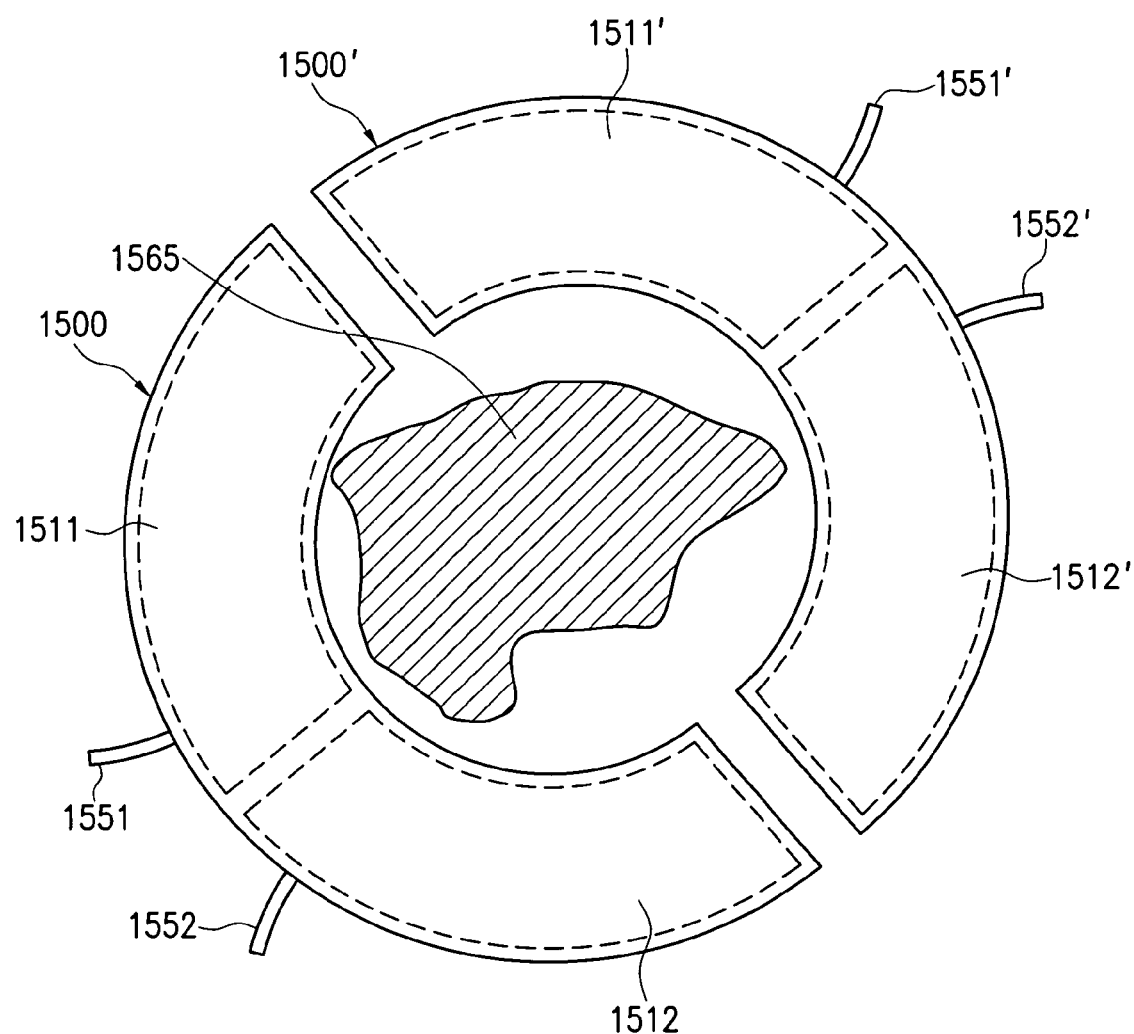
FIG. 16 is a schematic diagram of an area of treatment showing the electrode arrangements of FIG. 15 placed around a wound.

FIG. 16 is a schematic view of an area of treatment in which electrode arrangements according to the eighth embodiment of the invention are placed around a wound 1565 of a human patient. Electrode arrangements 1500 and 1500' are placed on the skin on diagonally opposite sides of the wound 1565 with the first surface of the substrate 1520 of each electrode arrangement arranged to face the skin. Each electrode arrangement is pressed against the skin in order to adhere the adhesive sealing gel 1531 and 1532 around each electrode 1511 and 1512, respectively, to the skin. This creates a seal preventing the ingress of moisture to any exposed conductive components of the electrode arrangements. Connectors 1551 and 1552 provide electrical signals to electrodes 1511 and 1512 respectively from an electrical generator (not shown) and connectors 1551' and 1552' provide electrical signals to electrodes 1511' and 1512'. electrical current can therefore be applied between different electrodes passing through different paths through the regenerative tissue under the wound. For example electrical current may be applied to pass from electrode 1511 to electrode 1512' and electrical current may pass from electrode 1512 to electrode 1511'. The current may be applied to flow in the opposite direction. Alternatively, electrical current may be applied to pass from electrode 1511 to electrode 1511' and from electrode 1512 to electrode 1512'. The current may be applied to flow simultaneously in opposing directions under the wound. For example the current may be applied to flow from electrode 1511 to electrode 1512' and from electrode 1511' to electrode 1512.

Figure 17:
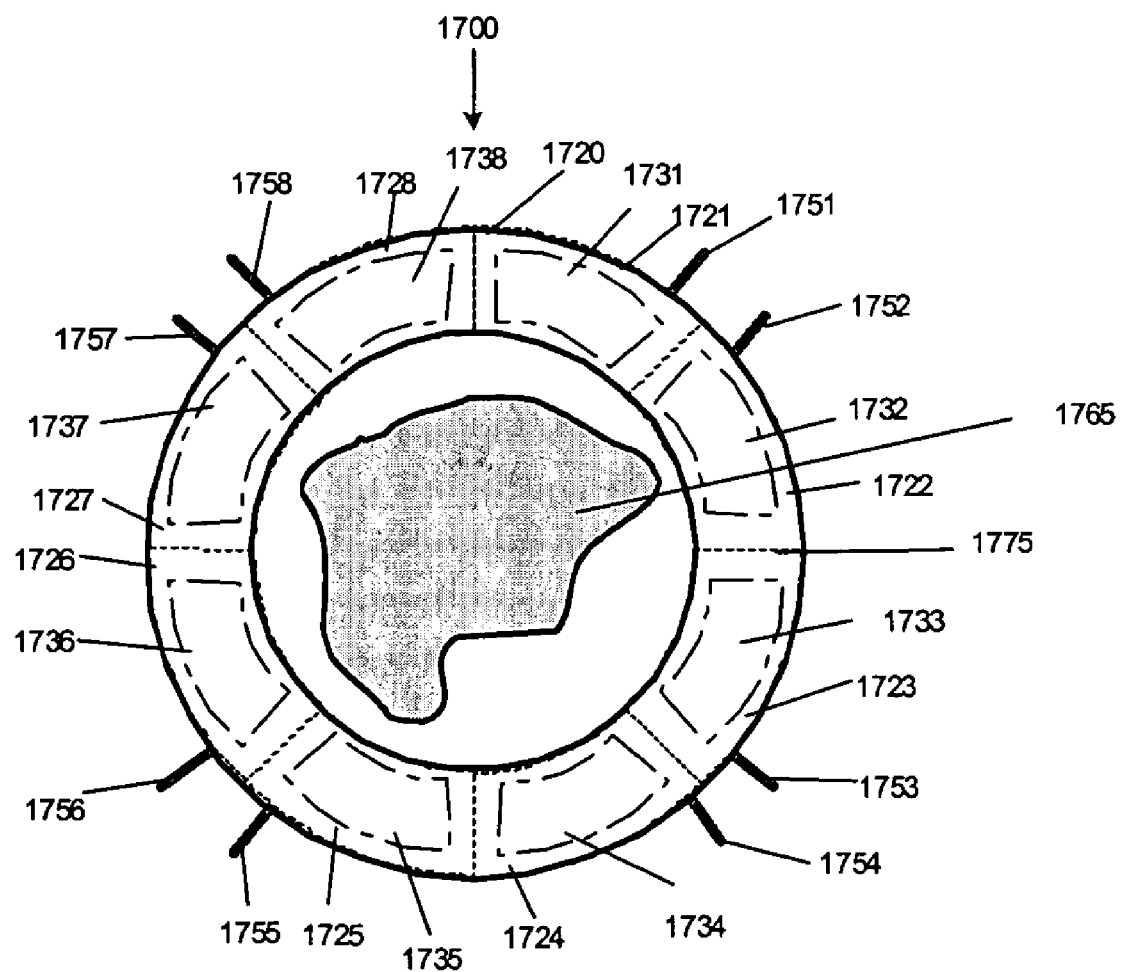
FIG. 17 is a schematic diagram of an electrode arrangement according to an ninth embodiment of the invention.

FIG. 17 is a schematic diagram of a second side of an electrode arrangement according to a ninth embodiment of the invention. The electrode arrangement is placed in an area of treatment around a wound 1765. The electrode arrangement 1700 comprises a substrate 1720 in the form of an annulus. The substrate is subdivided along the radial axes into 8 substantially equally sized portions 1721, 1722, 1723, 1724, 1725, 1726, 1727 and 1728 positioned around the aperture of the annulus. Each portion has a conductive area on a first surface of the substrate opposed to the second surface, these are shown as dotted areas 1731, 1732, 1733, 1734, 1735, 1736, 1737 and 1738, respectively. Each conductive area is made up of mesh structure of conductive tracks and a conductive gel. Perforations 1775 disposed radially between adjacent portions allow one or more of portions 1721, 1722, 1723, 1724, 1725, 1726, 1727 and 1728 to be removed. This arrangement allows portions of the substrate to be removed to facilitate treatment of different size and shapes of wounds. Connectors 1751, 1752, 1753, 1754, 1755, 1756, 1757, 1758 provide electrical signals to electrodes 1721, 1722, 1723, 1724, 1725, 1726, 1727 and 1728, respectively, when connected to an electrical generator.

Although the common substrate in this embodiment is in the form of a ring, the common substrate may in the form of any shape with an aperture in the central region of the substrate.

It may be appreciated that while in this embodiment, the common substrate completely surrounds the wound, in alternative embodiments the common substrate may be part annular and partially surround the wound.

Although in this embodiment the substrate is divided into 8 portions it may be understood that the substrate may be subdivided into any number of portions. Furthermore, although perforations are provided along the borders between adjacent portions in this embodiment, in alternative embodiments perforations may not be present and the substrate may be cut or broken along a radial line to remove portions.

Figure 18:
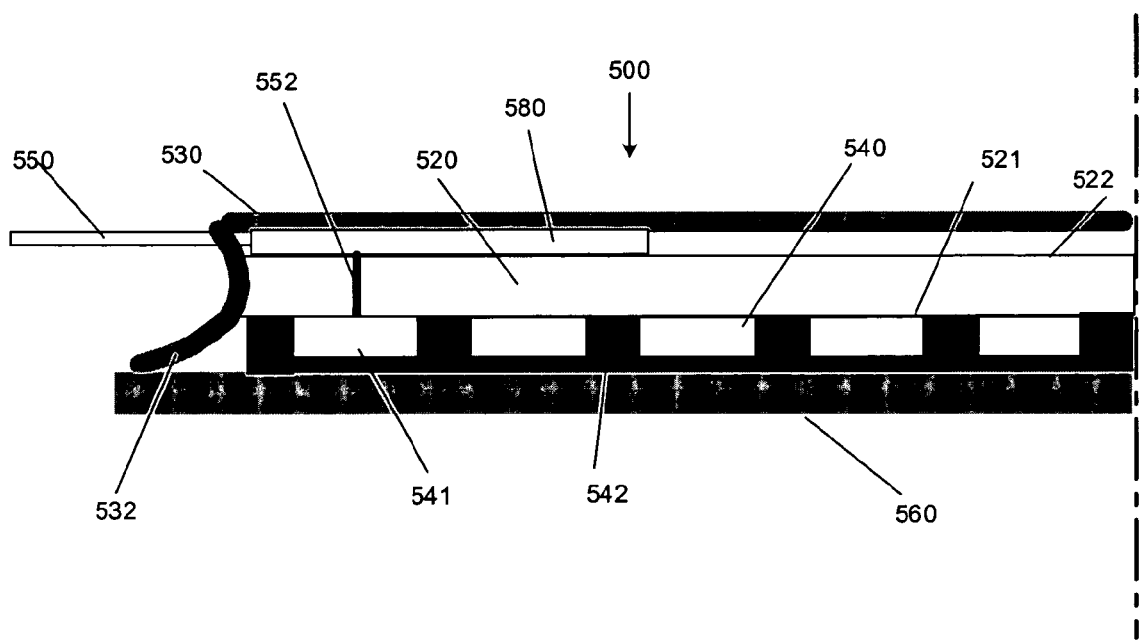
FIG. 18 is a cross sectional diagram of an electrode arrangement according to a tenth embodiment of the invention.

FIG. 18 is a partial cross-sectional view of an electrode arrangement 500 according to a tenth embodiment of the invention. The electrode arrangement 500 comprises a printed circuit board 520 having a first surface 521 and a second surface 522 opposed to the first surface, electrically non-conductive waterproof sealing pad 530, an electrode 540 for applying electrical signals to the skin 560 when placed in contact with the skin and an electrical generator circuit 580. The electrode 540 is provided on the first surface of the printed circuit board 520 and comprises electrically conductive tracks 541 and electrically conductive gel 542 to provide electrical conductivity across a portion of the surface of the printed circuit board. The electrical generator circuit 580 is placed on the second surface of the printed circuit board 520 and connector 552 provides an electrically conductive connection between the electrical generator circuit 580 and electrode 540 through the printed circuit board 520. Electrical lead 550 can be used to connect the electrode arrangement to another electrode arrangement. The sealing pad 530 is placed over the second surface of the printed circuit board 520. The outer edges 532 on one surface of the sealing pad 530 have adhesive properties and the sealing pad 530 is positioned such that the edges 532 of the sealing pad extend beyond the edges of the printed circuit board 520 and adhere the electrode arrangement to the skin. Such an arrangement prevents ingress of moisture such as sweat, urine or blood to the electrode 540 when the electrode arrangement 500 is placed on the skin and to the electrical generator circuit 580 and the electrical connection between the electrical generator circuit and the electrical lead 550. The electrical generator 580 contains the circuitry shown in FIG. 9A and has a surface area small enough to fit on the back of the printed circuit board. The thickness of the electrical generator 580 is approximately 6 mm. The small size of the electrical generator allows it to be easily integrated onto the printed circuit board providing a small and compact electrode arrangement.

While in this embodiment the generator is described as having a thickness of approximately 6 mm, it may be appreciated that the electrical generator may be of any size that fits on the back of the electrode and that can be carried comfortably by the patient.

Figure 19:
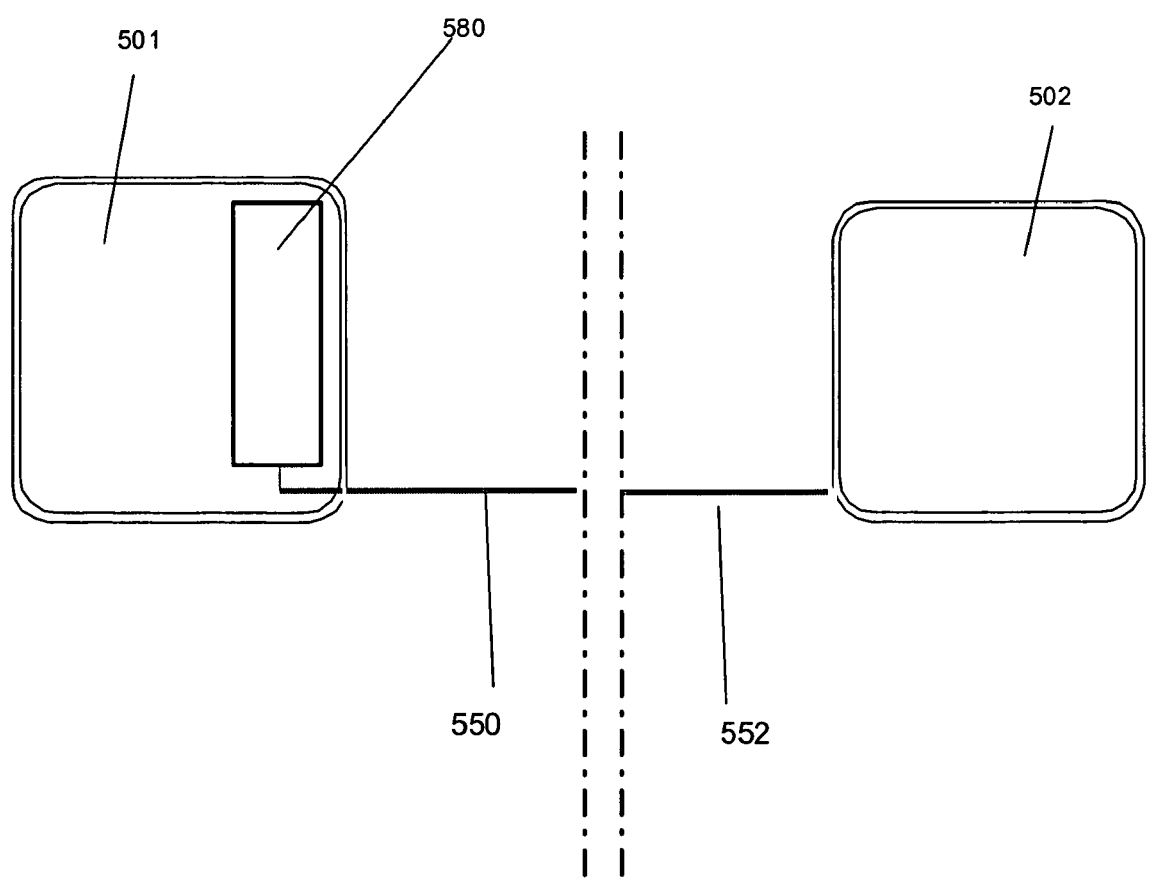
FIG. 19 is a schematic diagram of the electrode arrangement of FIG. 18 connected to another electrode arrangement.

FIG. 19 is a schematic view of the embodiment of the electrode arrangement 501 shown in FIG. 18 connected to another electrode arrangement 502. Current from electrical generator 580 is applied across electrode arrangements 501 and 502 through connectors 550 and 552.

It may be appreciated that although in this embodiment electrical generator 580 is connected to one other electrode arrangement it may be connected to any number of electrode arrangements to apply current between electrode arrangement 501 and any number of electrode arrangements.

Figure 20:
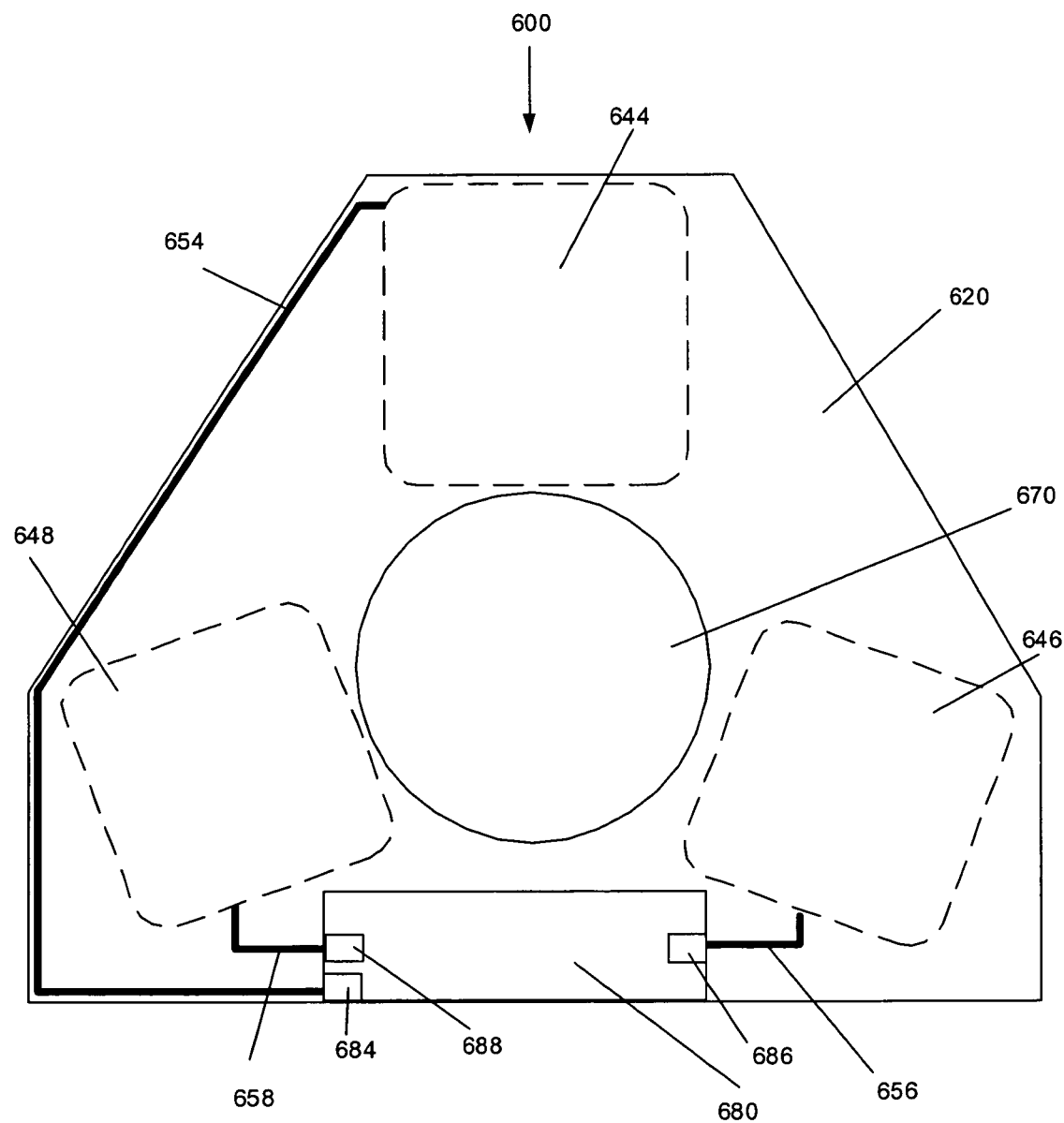
FIG. 20 is a schematic diagram of an electrode arrangement according to an eleventh embodiment of the invention.

FIG. 20 is a schematic view of a second side of an electrode arrangement according to a eleventh embodiment of the invention. The electrode arrangement 600 comprises a common printed circuit board 620 and three electrodes provided on the first surface 621 of the printed circuit board 620 which are shown in the figure as dotted areas 644, 646 and 648. An aperture 670 is located in the central region of the printed circuit board 620. The electrodes 644, 646 and 648 are arranged around the aperture 670. Each electrode is electrically isolated from another electrode. An electrical generator circuit 680 is provided on the second surface of the electrode arrangement 600. Connectors 654, 656, and 658 provide electrical signals from output ports 684, 686, and 688 of the electrical generator circuit 680 to the electrodes 644, 646, and 648, respectively. An annulus of electrically non-conductive sealing gel is disposed around the edges of the aperture 670 on the first surface 621 of the electrode arrangement to prevent the ingress of moisture into the electrode arrangement 600. A waterproof sticky plaster (not shown in the Figure) is placed over the second surface of the electrode arrangement to cover the substrate 620 and the generator 680 sealing the electrode arrangement 600 to skin when placed on the skin and preventing the ingress of moisture to any exposed components. This arrangement has the advantage that the electrode arrangement is completely self contained and does not need to be connected to an external electrical generator circuit. Such an arrangement may be disposable after use.

Figure 21:
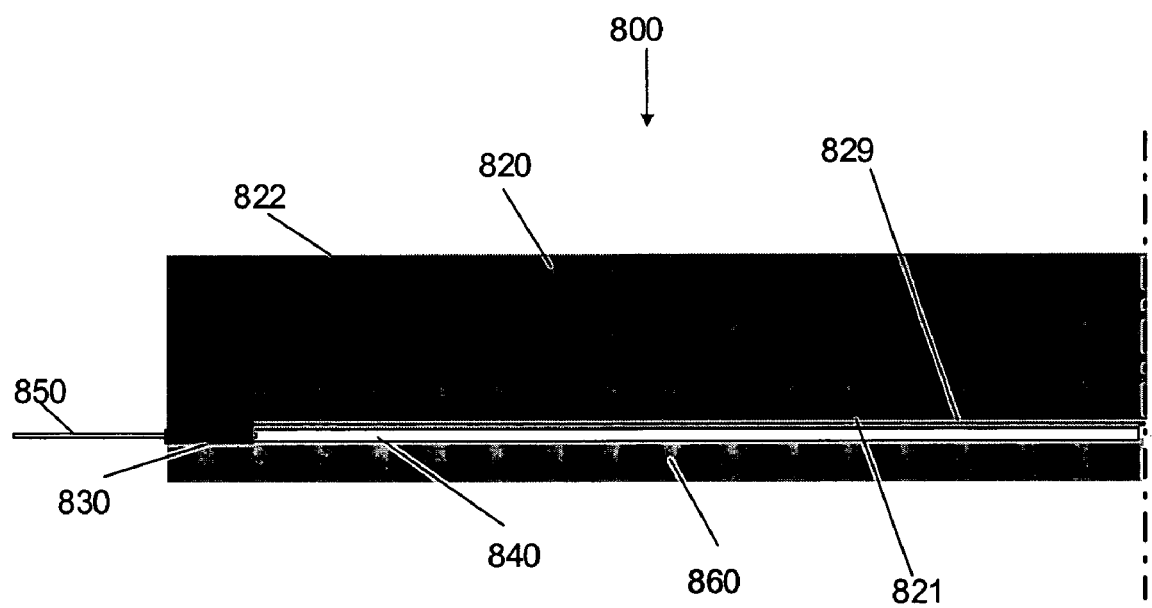
FIG. 21 is a partial cross sectional diagram of an electrode arrangement according to an twelfth embodiment of the invention.

FIG. 21 is a partial cross sectional view of an electrode arrangement 800 placed on the skin 860 of a patient according to a twelfth embodiment of the present invention. The electrode arrangement 800 comprises a porous layer of foam 820 having a first surface 821 and a second surface 822 opposed to the first surface, an electrode 840 for applying electrical signals to the skin 860 when placed in contact with the skin and an electrically conductive lead 850 for supplying electrical signals to the electrode 840. A layer of electrically insulating, waterproof, adhesive material 829 is disposed on the first surface of the foam layer and adheres the electrode 840 to the foam layer 820 and prevents the ingress of moisture from the foam layer 820 to the electrode 840. Waterproof, electrical insulating, adhesive material is disposed on the outermost edges of the first surface 821 and around the electrically conductive lead 850, forming a seal 830 adhering the electrode arrangement to the skin and preventing the ingress of moisture to any exposed conductive elements of the electrode arrangement. Such an arrangement provides an electrode arrangement which is easy to apply and an overall structure which remains effective for longer. In addition, the layer of foam absorbs excess fluids from outside the electrode arrangement.

Figure 22:
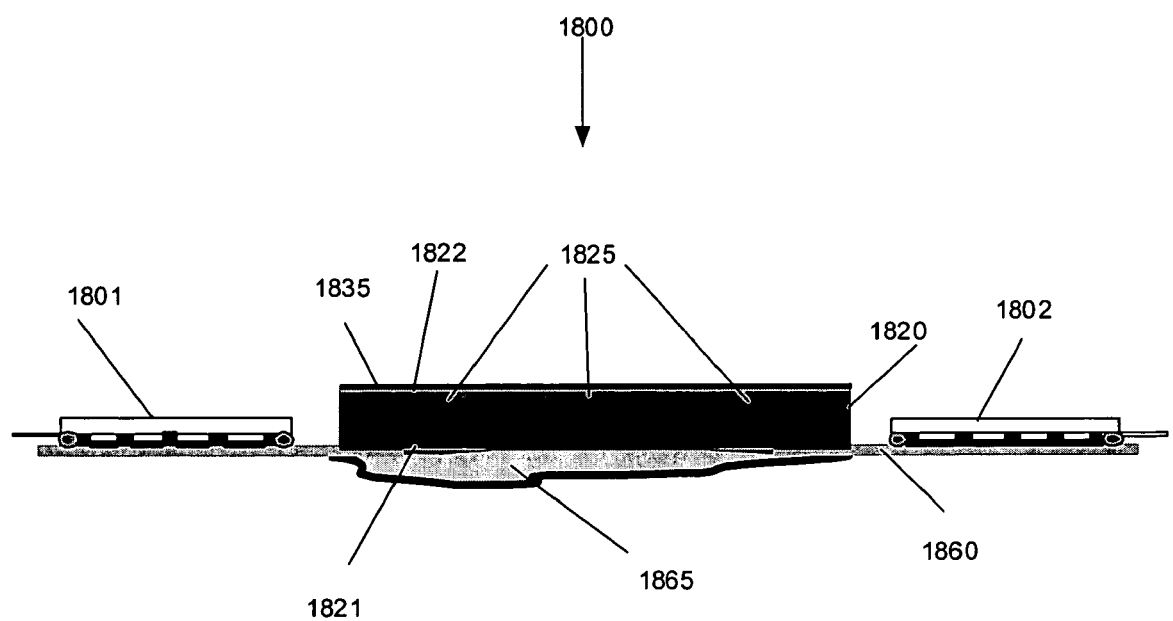
FIG. 22 is a partial cross-sectional diagram of a pad for use with one or more electrode arrangements according to any of the embodiments of the invention.

FIG. 22 is a partial cross sectional view of a pad for use with one or more electrode arrangements according to any of the embodiments of the invention. The pad 1800 comprises a layer of absorbent foam 1820 having a first surface 1821 and a second surface 1822 opposed to the first surface. A plurality of trenches 1825 is arranged in a honeycomb grid structure across the layer of foam 1820. The depth of the trenches extends from the second surface 1822 of the layer of foam 1820 to the first surface 1821. The trenches 1825 are filled with an electrically insulating material. A layer of electrically insulating, adhesive material 1835 is disposed on the second surface of the foam layer 1820. The pad 1800 is placed over a wound 1865. An electrode arrangement 1801 for applying electrical signals to the skin is placed in contact with the skin on side of the device 1800, and another electrode arrangement 1802 is placed in contact with the skin on the other side of the pad opposite the first electrode arrangement 1801. The layer of foam 1820 provides an absorbent medium for absorbing fluid from the wound 1865. The trenches of insulating material 1825 provide a barrier to any electrical conductive path which may be created through the layer of foam 1820 by the presence of the exuded fluid in the foam. Such an arrangement helps to eliminate any low resistance path which may be created from the exuded fluid and which would otherwise short circuit current that should be passing through the regenerative tissues under the wound.

Figure 23:
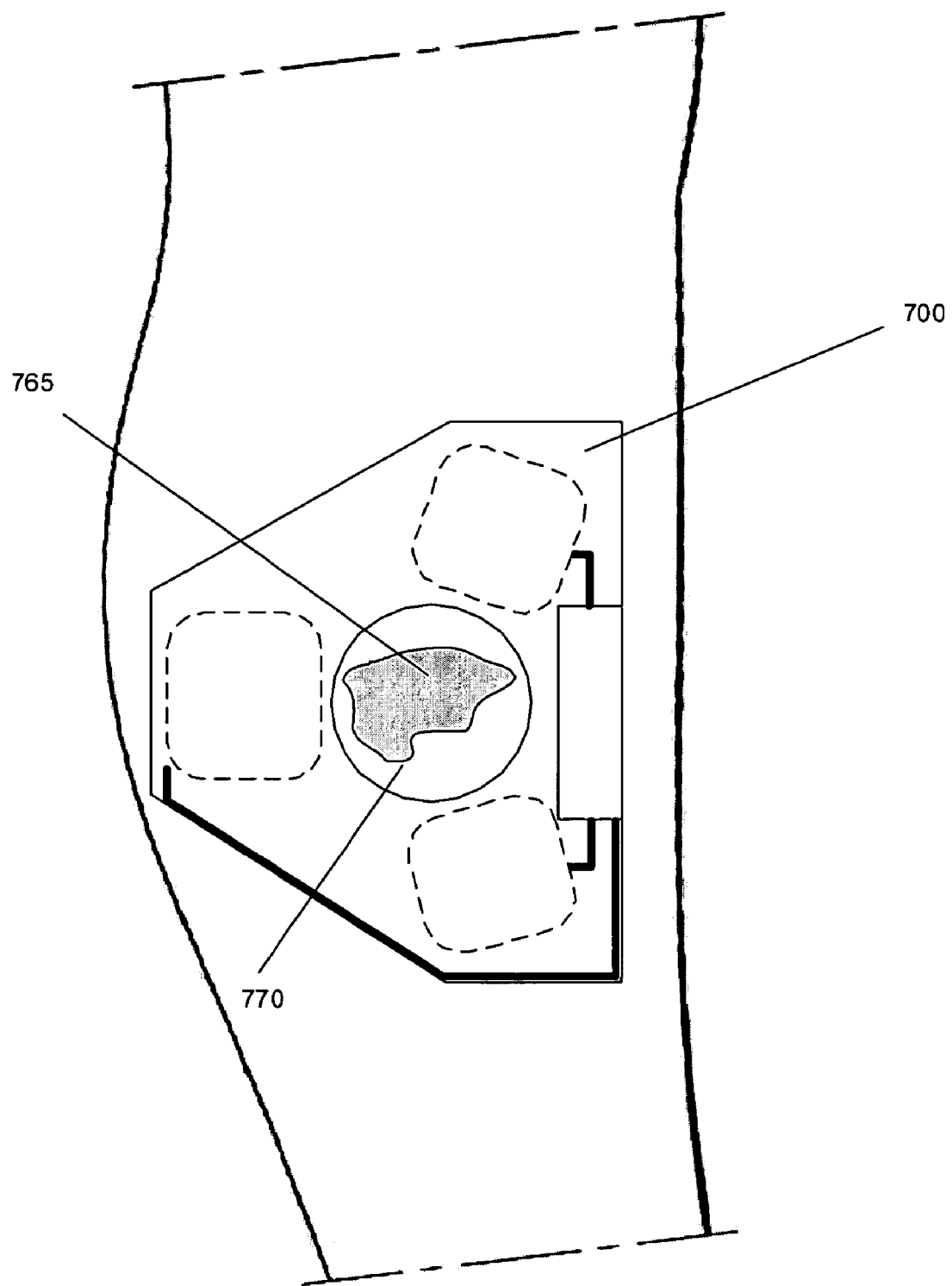
FIG. 23 is a schematic diagram of a treatment area showing the electrode arrangement of FIG. 20 disposed around a wound.

FIG. 23 is a schematic view of an area of treatment on the leg of a patient in which an electrode arrangement 700 of FIG. 20 is placed around a wound 765 such that the aperture 770 is placed over the wound 765.

Although in the above embodiments, the electrically conductive tracks or elements are etched out of gold plated copper, it may be appreciated that they may be etched out of any electrically conductive material. Furthermore, it may be appreciated that the electrically conductive tracks are etched in the form of a honey comb mesh pattern, it may be appreciated that any mesh or grid pattern or other any pattern of tracks allowing flexibility of the electrode arrangement may be used. It may also be appreciated that any type of flexible substrate may be used in place of a printed circuit board.

Although in FIG. 1, electrically non-conductive sealing gel placed around the edges of the printed circuit board is used to seal the electrode arrangement to the skin, in other embodiments a waterproof adhesive material may be placed over the second surface of the printed surface board to adhere the electrode arrangement to the skin.

In alternative embodiments, the electrode arrangement of FIG. 1 may include an electrical generator on the second surface of the printed circuit board. The electrical generator may be sealed by covering it with a waterproof sealing pad or alternatively the generator may be contained within a sealed unit.

Although in the embodiment of FIG. 4, the electrically conductive elements are square shaped, it should be appreciated that they may have any geometrical shape.

Although in the embodiment of FIG. 5 electrically non-conductive sealing gel placed around the edges of the printed circuit board is used to seal the electrode arrangement to the skin, in other embodiments a waterproof adhesive material may be placed over the second surface of the printed surface board to adhere the electrode arrangement to the skin.

In alternative embodiments, the electrode arrangement of FIG. 5 may include an electrical generator on the second surface of the printed circuit board. The electrical generator may be sealed by covering it with a waterproof sealing pad or alternatively it may be contained within a sealed unit.

It may be appreciated that the different embodiments of electrode arrangements may be connected to any type of external electrical generator circuit providing current.

Although in FIG. 10, connectors 251, 252 and 253 protrude from the top of the bandage for connection to the electrical generator, in alternative embodiments the connectors may protrude from the bandage at any level of the bandage. Alternatively the treatment area may not be bandaged. In further embodiments, the electrical generator may not be attached to the leg.

Although in FIG. 18, electrical connection between the electrode and the electrical generator is made by a connector through the printed circuit board, in alternative embodiments electrical connection may be made between the electrode and the electrical generator through a connector passing by the exterior of the printed circuit board.

Although the embodiment of FIG. 21 has only one electrode, in alternative embodiments, two or more electrodes may be provided on the foam layer.

The present invention has applicability for any animal but can be particularly used on humans.

Although the present invention has been described with reference to specific embodiments, it will be apparent to a skilled person in the art that modifications lie within the spirit and scope of the present invention.

What is claimed is:

1. An electrode arrangement for applying electrical signals to skin of an animal, comprising:
   a plurality of flexible electrically non-conductive substrates; and
   one or more flexible planar electrodes provided on a first surface of each of the substrates for applying electrical signals to the skin when placed on the skin;
   wherein each said flexible planar electrode, when in said planar configuration, comprises a concave edge and a convex edge defining at least part of a crescent shape or a shape corresponding to a cross-section of at least a partial annulus;
   wherein the one or more flexible planar electrodes comprises a plurality of interconnected electrically conductive elements to form a two-dimensional electrically conductive path across at least a portion of the first surface of the substrate; and
   wherein the plurality of interconnected electrically conductive elements are arranged in a matrix to allow flexion of the electrode arrangement.

2. An electrode arrangement according to claim 1, wherein electrically conductive gel is provided on the or each electrode to provide an electrically conductive path to the skin.

3. An electrode arrangement according to claim 1, wherein electrical components are provided on a second surface of the substrate opposed to said first surface.

4. An electrode arrangement according to claim 1, further comprising an electrical generator circuit on a second surface of the substrate opposed to said first surface for applying current to at least one said electrode via a respective at least one said connector.

5. An apparatus for treating a wound comprising the electrode arrangement of claim 1 and an electric generator circuit for applying current to at least one said electrode via a respective at least one said connector.

6. An electrode arrangement according to claim 4, comprising at least three electrodes and three connectors, wherein the electric generator circuit is adapted to switch current to flow between different electrodes of the at least three electrodes.

7. An electrode arrangement according to claim 4, wherein the electrical generator circuit is adapted to switch the direction of the current between electrodes.

8. An electrode arrangement according to claim 1, wherein the substrate is porous.

9. An electrode arrangement according to claim 1, wherein one or more elements of highly electrical resistant material is provided on a surface of the or each electrode.

10. An electrode arrangement according to claim 9 wherein the one or more elements of highly resistant material are interspaced by elements of electrically insulating material.

11. An electrode arrangement according to claim 1, wherein the substrate includes an extended portion comprising at least one electrically conductive region, each of the electrically conductive regions being in electrical contact with a respective electrode to form a connector to said electrode.

12. An electrode arrangement for applying electrical signals to skin of an animal comprising:
a flexible electrically non-conductive substrate;
a plurality of electrodes on a first surface of the substrate for applying electrical signals to the skin when placed on the skin;
wherein a plurality of elements of electrically conductive gel is provided on the or each electrode to provide an electrically conductive path to the skin;
wherein a plurality of elements of highly electrical resistant material are provided on a surface of the or each electrode between the surface of the electrode and respective elements of gel; and
wherein the plurality of elements of conductive gel and the plurality of elements of highly resistant material are interspaced on each electrode by elements of electrically insulating material.

13. An electrode arrangement according to claim 12, wherein the or each electrode comprises a plurality of interconnected electrically conductive elements to form a two-dimensional electrically conductive path across at least a portion of the first surface of the substrate.

14. An electrode arrangement according to claim 13, wherein the plurality of interconnected electrically conductive elements are arranged in a matrix to allow flexion of the electrode arrangement.

15. An electrode arrangement according to claim 13, wherein the plurality of interconnected electrically conductive elements are arranged in a mesh pattern to allow flexion of the electrode arrangement.

16. An electrode arrangement according to claim 12, wherein the substrate is a planar substrate with a convex edge along a first side and a concave edge along a second side, the first side opposite the second side on the substrate.

17. An electrode arrangement according to claim 12, wherein the substrate is porous.

18. An electrode arrangement according to claim 12, further comprising an electrical generator circuit on a second surface of the said substrate opposed to the first surface of said substrate to apply electrical signals to said plurality of electrodes.

19. An electrode arrangement according to claim 18, comprising at least three electrodes, wherein the electrical generator circuit is adapted to switch current to flow between different electrodes of the at least three electrodes.

20. An electrode arrangement according to claim 18, wherein the electrical generator circuit is adapted to switch the direction of the current between electrodes.

21. An electrode arrangement according to claim 18, wherein the electrical generator circuit comprises a waveform generator for generating current waveforms across said electrodes.

22. An electrode arrangement for applying electrical signals according to claim 21, wherein the waveform generator is pre-programmed with one or more programs to generate a pre-determined waveform or a pre-determined sequence of pre-determined waveforms.

23. An electrode arrangement according to claim 18, wherein the electrical generator circuit is arranged to switch current between pairs of electrodes.

24. A device for absorbing fluid from a wound for use with an apparatus for treating a wound comprising:
a flexible electrically non-conductive substrate;
a plurality of electrodes on a first surface of the substrate for arranging around the wound;
a plurality of connectors each connected to a respective electrode adapted to allow current to flow to each of the plurality of electrodes when connected to a current generator, the device comprising:
one or more elements of absorbent material; and
a plurality of interconnected portions of electrically insulating material interposed between the elements of absorbent material.

* * * * *